United States Patent
Shemi et al.

(10) Patent No.: US 9,080,173 B2
(45) Date of Patent: Jul. 14, 2015

(54) METHODS AND COMPOSITIONS FOR RNAI-BASED CANCER TREATMENT

(71) Applicant: SILENSEED LTD., Jerusalem (IL)

(72) Inventors: Amotz Shemi, Herzeliya (IL); Elina Zorde Khvalevsky, Jerusalem (IL)

(73) Assignee: SILENSEED LTD., Jerusalem (IL)

( * ) Notice: Subject to any disclaimer, the term of this patent is extended or adjusted under 35 U.S.C. 154(b) by 0 days.

(21) Appl. No.: 14/526,642

(22) Filed: Oct. 29, 2014

(65) Prior Publication Data
US 2015/0050341 A1 Feb. 19, 2015

Related U.S. Application Data

(62) Division of application No. 13/451,231, filed on Apr. 19, 2012, now Pat. No. 8,889,642.

(51) Int. Cl.
| | | |
|---|---|---|
| *A01N 43/04* | (2006.01) | |
| *A61K 31/70* | (2006.01) | |
| *C12N 15/113* | (2010.01) | |
| *A61K 31/713* | (2006.01) | |
| *A61K 31/7105* | (2006.01) | |
| *A61K 31/7115* | (2006.01) | |
| *A61K 9/00* | (2006.01) | |
| *A61K 47/34* | (2006.01) | |

(52) U.S. Cl.
CPC ............ *C12N 15/113* (2013.01); *A61K 9/0024* (2013.01); *A61K 31/713* (2013.01); *A61K 31/7105* (2013.01); *A61K 31/7115* (2013.01); *A61K 47/34* (2013.01); *C12N 15/1135* (2013.01); *C12N 2310/11* (2013.01); *C12N 2310/14* (2013.01)

(58) Field of Classification Search
None
See application file for complete search history.

(56) References Cited

U.S. PATENT DOCUMENTS

| | | |
|---|---|---|
| 2005/0176045 A1 | 8/2005 | Fedorov et al. |
| 2008/0124370 A1 | 5/2008 | Marx |
| 2010/0286241 A1 | 11/2010 | Xie |
| 2011/0195123 A1 | 8/2011 | Shemi |
| 2011/0275891 A1 | 11/2011 | Shemi |

FOREIGN PATENT DOCUMENTS

| | | |
|---|---|---|
| WO | 2009/108217 | 9/2009 |
| WO | 2010/001325 | 1/2010 |
| WO | 2011/062503 | 5/2011 |

OTHER PUBLICATIONS

Brummelkamp et al. "Stable suppression of tumorigenicity by virus-mediated RNA interference" Cancer Cell, vol. 2, No. 3, pp. 243-247 (Sep. 2002).
Fleming et al. "Molecular consequences of silencing mutant K-ras in pancreatic cancer cells: Justification for K-ras-directed therapy" Molecular Cancer Research, vol. 3, No. 7, pp. 413-423 (Jul. 2005).
Makadia & Siegel "Poly lactic-co-glycolic acid (PLGA) as biodegradable controlled drug delivery carrier" Polymers, vol. 3, No. 3, pp. 1377-1397 (Aug. 2011).
Morioka et al. "Suppression of invasion of a hamster pancreatic cancer cell Line by antisense oligonucleotides mutation-matched to K-ras gene" In Vivo, vol. 19, No. 3, pp. 535-538 (May-Jun. 2005).
Normanno et al. "Implications for KRASstatus and EGFR-targeted therapies in metastatic CRC" Nature Reviews Clinical Oncology, vol. 6, No. 9, pp. 519-527 (Sep. 2009).
Park et al. "Biodegradable polymers for microencapsulation of drugs" Molecules, vol. 10, No. 1, pp. 146-161 (Jan. 2005).
Rejiba et al. "K-ras oncogene silencing strategy reduces tumor growth and enhances gemcitabine chemotherapy efficacy for pancreatic cancer treatment" Cancer Science, vol. 98, No. 7, pp. 1128-1136 (Jul. 2007).
Singh et al. "A gene expression signature associated with 'K-ras addiction' reveals regulators of EMT and tumor cell survival" Cancer Cell, vol. 15, No. 6, pp. 489-500 (Jun. 2009).
Wang et al. "Identification of effective siRNA against K-ras in human pancreatic cancer cell line MiaPaCa-2 siRNA expression cassette" World J. Gastroenterology, vol. 11, No. 13, pp. 2026-2031 (Apr. 2005).

*Primary Examiner* — Jennifer McDonald
(74) *Attorney, Agent, or Firm* — JMB Davis Ben-David

(57) ABSTRACT

The present invention generally concerns methods and compositions for treating mutated K-ras expressing cancers.

12 Claims, 8 Drawing Sheets

| NUMBER | STABILITY | | | | EFFICACY AT 120h |
|---|---|---|---|---|---|
| | 24h | 1W | 2W | 4W | |
| siKRAS G12D | | | | | 4 |
| siKRAS G12D-1 | | | | | 2 |
| siKRAS G12D-2 | | | | | 1 |
| siKRAS G12D-3 | | | | | 2 |
| siKRAS G12D-4 | | | | | 4 |
| siKRAS G12D-5 | | | | | 3 |
| siKRAS G12D-6 | | | | | 3 |

Figure 6

| NUMBER | STABILITY | | | | EFFICACY AT 120h |
|---|---|---|---|---|---|
| | 24h | 1W | 2W | 4W | |
| siKRAS G12D | | | | | 4 |
| siKRAS G12D-7 | | | | | 3 |
| siKRAS G12D-8 | | | | | 3 |
| siKRAS G12D-9 | | | | | 3 |
| siKRAS G12D-10 | | | | | 3 |
| siKRAS G12D-11 | | | | | 2 |

Figure 6 cont'd

| NUMBER | STABILITY | | | | EFFICACY AT 120h |
|---|---|---|---|---|---|
| | 24h | 1W | 2W | 4W | |
| siKRAS G12D | | | | | 4 |
| siKRAS G12D-12 | | | | | 1 |
| siKRAS G12D-13 | | | | | 2 |
| siKRAS G12D-14 | | | | | 3 |
| siKRAS G12D-15 | | | | | 2 |

Figure 6 cont'd 2

SEQUENCE LISTING

```
<160> NUMBER OF SEQ ID NOS: 68

<210> SEQ ID NO 1
<211> LENGTH: 16
<212> TYPE: RNA
<213> ORGANISM: Artificial Sequence
<220> FEATURE:
<223> OTHER INFORMATION: siRNA sequence

<400> SEQUENCE: 1
guuggagcug auggcg                                                    16

<210> SEQ ID NO 2
```

```
<211> LENGTH: 16
<212> TYPE: RNA
<213> ORGANISM: Artificial Sequence
<220> FEATURE:
<223> OTHER INFORMATION: siRNA sequence

<400> SEQUENCE: 2
guuggagcug uuggcg                                                         16

<210> SEQ ID NO 3
<211> LENGTH: 16
<212> TYPE: RNA
<213> ORGANISM: Artificial Sequence
<220> FEATURE:
<223> OTHER INFORMATION: siRNA sequence

<400> SEQUENCE: 3
guuggagcug cuggcg                                                         16

<210> SEQ ID NO 4
<211> LENGTH: 16
<212> TYPE: RNA
<213> ORGANISM: Artificial Sequence
<220> FEATURE:
<223> OTHER INFORMATION: siRNA sequence

<400> SEQUENCE: 4
guuggagcua guggcg                                                         16

<210> SEQ ID NO 5
<211> LENGTH: 16
<212> TYPE: RNA
<213> ORGANISM: Artificial Sequence
<220> FEATURE:
<223> OTHER INFORMATION: siRNA sequence

<400> SEQUENCE: 5
guuggagcuu guggcg                                                         16

<210> SEQ ID NO 6
<211> LENGTH: 16
<212> TYPE: RNA
<213> ORGANISM: Artificial Sequence
<220> FEATURE:
<223> OTHER INFORMATION: siRNA sequence

<400> SEQUENCE: 6
guuggagcug gugacg                                                         16

<210> SEQ ID NO 7
<211> LENGTH: 16
<212> TYPE: RNA
<213> ORGANISM: Artificial Sequence
<220> FEATURE:
<223> OTHER INFORMATION: siRNA sequence

<400> SEQUENCE: 7
guuggagcug guugcg                                                         16

<210> SEQ ID NO 8
<211> LENGTH: 14
<212> TYPE: RNA
<213> ORGANISM: Artificial Sequence
<220> FEATURE:
<223> OTHER INFORMATION: siRNA sequence

<400> SEQUENCE: 8
```

```
uaggcaagag ugcc                                                            14

<210> SEQ ID NO 9
<211> LENGTH: 19
<212> TYPE: RNA
<213> ORGANISM: Artificial Sequence
<220> FEATURE:
<223> OTHER INFORMATION: siRNA sequence

<400> SEQUENCE: 9
guuggagcug auggcguag                                                       19

<210> SEQ ID NO 10
<211> LENGTH: 19
<212> TYPE: RNA
<213> ORGANISM: Artificial Sequence
<220> FEATURE:
<223> OTHER INFORMATION: siRNA sequence

<400> SEQUENCE: 10
guuggagcug uuggcguag                                                       19

<210> SEQ ID NO 11
<211> LENGTH: 19
<212> TYPE: RNA
<213> ORGANISM: Artificial Sequence
<220> FEATURE:
<223> OTHER INFORMATION: siRNA sequence

<400> SEQUENCE: 11
guuggagcug cuggcguag                                                       19

<210> SEQ ID NO 12
<211> LENGTH: 19
<212> TYPE: RNA
<213> ORGANISM: Artificial Sequence
<220> FEATURE:
<223> OTHER INFORMATION: siRNA sequence

<400> SEQUENCE: 12
guuggagcua guggcguag                                                       19

<210> SEQ ID NO 13
<211> LENGTH: 19
<212> TYPE: RNA
<213> ORGANISM: Artificial Sequence
<220> FEATURE:
<223> OTHER INFORMATION: siRNA sequence

<400> SEQUENCE: 13
guuggagcuu guggcguag                                                       19

<210> SEQ ID NO 14
<211> LENGTH: 19
<212> TYPE: RNA
<213> ORGANISM: Artificial Sequence
<220> FEATURE:
<223> OTHER INFORMATION: siRNA sequence

<400> SEQUENCE: 14
guuggagcug gugacguag                                                       19

<210> SEQ ID NO 15
<211> LENGTH: 19
<212> TYPE: RNA
```

```
<213> ORGANISM: Artificial Sequence
<220> FEATURE:
<223> OTHER INFORMATION: siRNA sequence

<400> SEQUENCE: 15
guuggagcug guugcguag                                                    19

<210> SEQ ID NO 16
<211> LENGTH: 17
<212> TYPE: RNA
<213> ORGANISM: Artificial Sequence
<220> FEATURE:
<223> OTHER INFORMATION: siRNA sequence

<400> SEQUENCE: 16
guuggagcug auggcgu                                                      17

<210> SEQ ID NO 17
<211> LENGTH: 18
<212> TYPE: RNA
<213> ORGANISM: Artificial Sequence
<220> FEATURE:
<223> OTHER INFORMATION: siRNA sequence

<400> SEQUENCE: 17
guuggagcug auggcgua                                                     18

<210> SEQ ID NO 18
<211> LENGTH: 19
<212> TYPE: RNA
<213> ORGANISM: Artificial Sequence
<220> FEATURE:
<223> OTHER INFORMATION: siRNA sequence

<400> SEQUENCE: 18
guuggagcug auggcguag                                                    19

<210> SEQ ID NO 19
<211> LENGTH: 20
<212> TYPE: RNA
<213> ORGANISM: Artificial Sequence
<220> FEATURE:
<223> OTHER INFORMATION: siRNA sequence

<400> SEQUENCE: 19
guuggagcug auggcguagg                                                   20

<210> SEQ ID NO 20
<211> LENGTH: 21
<212> TYPE: RNA
<213> ORGANISM: Artificial Sequence
<220> FEATURE:
<223> OTHER INFORMATION: siRNA sequence

<400> SEQUENCE: 20
guuggagcug auggcguagg c                                                 21

<210> SEQ ID NO 21
<211> LENGTH: 22
<212> TYPE: RNA
<213> ORGANISM: Artificial Sequence
<220> FEATURE:
<223> OTHER INFORMATION: siRNA sequence

<400> SEQUENCE: 21
guuggagcug auggcguagg ca                                                22
```

<210> SEQ ID NO 22
<211> LENGTH: 23
<212> TYPE: RNA
<213> ORGANISM: Artificial Sequence
<220> FEATURE:
<223> OTHER INFORMATION: siRNA sequence

<400> SEQUENCE: 22
guuggagcug auggcguagg caa                                          23

<210> SEQ ID NO 23
<211> LENGTH: 24
<212> TYPE: RNA
<213> ORGANISM: Artificial Sequence
<220> FEATURE:
<223> OTHER INFORMATION: siRNA sequence

<400> SEQUENCE: 23
guuggagcug auggcguagg caag                                         24

<210> SEQ ID NO 24
<211> LENGTH: 25
<212> TYPE: RNA
<213> ORGANISM: Artificial Sequence
<220> FEATURE:
<223> OTHER INFORMATION: siRNA sequence

<400> SEQUENCE: 24
guuggagcug auggcguagg caaga                                        25

<210> SEQ ID NO 25
<211> LENGTH: 26
<212> TYPE: RNA
<213> ORGANISM: Artificial Sequence
<220> FEATURE:
<223> OTHER INFORMATION: siRNA sequence

<400> SEQUENCE: 25
guuggagcug auggcguagg caagag                                       26

<210> SEQ ID NO 26
<211> LENGTH: 27
<212> TYPE: RNA
<213> ORGANISM: Artificial Sequence
<220> FEATURE:
<223> OTHER INFORMATION: siRNA sequence

<400> SEQUENCE: 26
guuggagcug auggcguagg caagagu                                      27

<210> SEQ ID NO 27
<211> LENGTH: 28
<212> TYPE: RNA
<213> ORGANISM: Artificial Sequence
<220> FEATURE:
<223> OTHER INFORMATION: siRNA sequence

<400> SEQUENCE: 27
guuggagcug auggcguagg caagagug                                     28

<210> SEQ ID NO 28
<211> LENGTH: 29
<212> TYPE: RNA
<213> ORGANISM: Artificial Sequence
<220> FEATURE:

```
<223> OTHER INFORMATION: siRNA sequence

<400> SEQUENCE: 28
guuggagcug auggcguagg caagagugc                                              29

<210> SEQ ID NO 29
<211> LENGTH: 30
<212> TYPE: RNA
<213> ORGANISM: Artificial Sequence
<220> FEATURE:
<223> OTHER INFORMATION: siRNA sequence

<400> SEQUENCE: 29
guuggagcug auggcguagg caagagugcc                                             30

<210> SEQ ID NO 30
<211> LENGTH: 16
<212> TYPE: RNA
<213> ORGANISM: Artificial Sequence
<220> FEATURE:
<223> OTHER INFORMATION: siRNA sequence

<400> SEQUENCE: 30
cgccaucagc uccaac                                                            16

<210> SEQ ID NO 31
<211> LENGTH: 16
<212> TYPE: RNA
<213> ORGANISM: Artificial Sequence
<220> FEATURE:
<223> OTHER INFORMATION: siRNA sequence

<400> SEQUENCE: 31
cgccaacagc uccaac                                                            16

<210> SEQ ID NO 32
<211> LENGTH: 16
<212> TYPE: RNA
<213> ORGANISM: Artificial Sequence
<220> FEATURE:
<223> OTHER INFORMATION: siRNA sequence

<400> SEQUENCE: 32
cgccagcagc uccaac                                                            16

<210> SEQ ID NO 33
<211> LENGTH: 16
<212> TYPE: RNA
<213> ORGANISM: Artificial Sequence
<220> FEATURE:
<223> OTHER INFORMATION: siRNA sequence

<400> SEQUENCE: 33
cgccacuagc uccaac                                                            16

<210> SEQ ID NO 34
<211> LENGTH: 16
<212> TYPE: RNA
<213> ORGANISM: Artificial Sequence
<220> FEATURE:
<223> OTHER INFORMATION: siRNA sequence

<400> SEQUENCE: 34
cgccacaagc uccaac                                                            16
```

```
<210> SEQ ID NO 35
<211> LENGTH: 16
<212> TYPE: RNA
<213> ORGANISM: Artificial Sequence
<220> FEATURE:
<223> OTHER INFORMATION: siRNA sequence

<400> SEQUENCE: 35
cgucaccagc uccaac                                                       16

<210> SEQ ID NO 36
<211> LENGTH: 16
<212> TYPE: RNA
<213> ORGANISM: Artificial Sequence
<220> FEATURE:
<223> OTHER INFORMATION: siRNA sequence

<400> SEQUENCE: 36
cgcaaccagc uccaac                                                       16

<210> SEQ ID NO 37
<211> LENGTH: 21
<212> TYPE: DNA
<213> ORGANISM: Artificial Sequence
<220> FEATURE:
<223> OTHER INFORMATION: siRNA sequence
<220> FEATURE:
<221> NAME/KEY: RNA
<222> LOCATION: (1)..(19)
<220> FEATURE:
<221> NAME/KEY: 2'-OMe
<222> LOCATION: (3)..(4)
<220> FEATURE:
<221> NAME/KEY: 2'-OMe
<222> LOCATION: (17)..(18)
<220> FEATURE:
<221> NAME/KEY: DNA
<222> LOCATION: (20)..(21)

<400> SEQUENCE: 37
guuggagcug auggcguagt t                                                 21

<210> SEQ ID NO 38
<211> LENGTH: 21
<212> TYPE: DNA
<213> ORGANISM: Artificial Sequence
<220> FEATURE:
<223> OTHER INFORMATION: siRNA sequence
<220> FEATURE:
<221> NAME/KEY: RNA
<222> LOCATION: (1)..(19)
<220> FEATURE:
<221> NAME/KEY: DNA
<222> LOCATION: (20)..(21)

<400> SEQUENCE: 38
cuacgccauc agcuccaact t                                                 21

<210> SEQ ID NO 39
<211> LENGTH: 19
<212> TYPE: RNA
<213> ORGANISM: Artificial Sequence
<220> FEATURE:
<223> OTHER INFORMATION: siRNA sequence
<220> FEATURE:
<221> NAME/KEY: 2-OMe
<222> LOCATION: (3)..(3)
<220> FEATURE:
<221> NAME/KEY: 2-OMe
<222> LOCATION: (9)..(9)
<220> FEATURE:
```

```
<221> NAME/KEY: 2-OMe
<222> LOCATION: (12)..(12)
<220> FEATURE:
<221> NAME/KEY: 2-OMe
<222> LOCATION: (17)..(17)

<400> SEQUENCE: 39
guuggagcug auggcguag                                          19

<210> SEQ ID NO 40
<211> LENGTH: 19
<212> TYPE: RNA
<213> ORGANISM: Artificial Sequence
<220> FEATURE:
<223> OTHER INFORMATION: siRNA sequence
<220> FEATURE:
<221> NAME/KEY: 2-OMe
<222> LOCATION: (2)..(2)
<220> FEATURE:
<221> NAME/KEY: 2-OMe
<222> LOCATION: (7)..(7)
<220> FEATURE:
<221> NAME/KEY: 2-OMe
<222> LOCATION: (10)..(10)
<220> FEATURE:
<221> NAME/KEY: 2-OMe
<222> LOCATION: (16)..(16)

<400> SEQUENCE: 40
cuacgccauc agcuccaac                                          19

<210> SEQ ID NO 41
<211> LENGTH: 21
<212> TYPE: DNA
<213> ORGANISM: Artificial Sequence
<220> FEATURE:
<223> OTHER INFORMATION: siRNA sequence
<220> FEATURE:
<221> NAME/KEY: RNA
<222> LOCATION: (1)..(19)
<220> FEATURE:
<221> NAME/KEY: DNA
<222> LOCATION: (20)..(21)

<400> SEQUENCE: 41
guuggagcug auggcguagt t                                       21

<210> SEQ ID NO 42
<211> LENGTH: 21
<212> TYPE: DNA
<213> ORGANISM: Artificial Sequence
<220> FEATURE:
<223> OTHER INFORMATION: siRNA sequence
<220> FEATURE:
<221> NAME/KEY: RNA
<222> LOCATION: (1)..(19)
<220> FEATURE:
<221> NAME/KEY: DNA
<222> LOCATION: (20)..(21)

<400> SEQUENCE: 42
cuacgccauc agcuccaact t                                       21

<210> SEQ ID NO 43
<211> LENGTH: 21
<212> TYPE: DNA
<213> ORGANISM: Artificial Sequence
<220> FEATURE:
<223> OTHER INFORMATION: siRNA sequence
<220> FEATURE:
<221> NAME/KEY: RNA
```

```
<222> LOCATION: (1)..(19)
<220> FEATURE:
<221> NAME/KEY: 2-OMe
<222> LOCATION: (3)..(3)
<220> FEATURE:
<221> NAME/KEY: 2-OMe
<222> LOCATION: (9)..(9)
<220> FEATURE:
<221> NAME/KEY: 2-OMe
<222> LOCATION: (12)..(12)
<220> FEATURE:
<221> NAME/KEY: 2-OMe
<222> LOCATION: (17)..(17)
<220> FEATURE:
<221> NAME/KEY: DNA
<222> LOCATION: (20)..(21)

<400> SEQUENCE: 43
guuggagcug auggcguagt t                                              21

<210> SEQ ID NO 44
<211> LENGTH: 21
<212> TYPE: DNA
<213> ORGANISM: Artificial Sequence
<220> FEATURE:
<223> OTHER INFORMATION: siRNA sequence
<220> FEATURE:
<221> NAME/KEY: RNA
<222> LOCATION: (1)..(19)
<220> FEATURE:
<221> NAME/KEY: 2'-OMe
<222> LOCATION: (2)..(2)
<220> FEATURE:
<221> NAME/KEY: 2'-OMe
<222> LOCATION: (7)..(7)
<220> FEATURE:
<221> NAME/KEY: 2'-OMe
<222> LOCATION: (10)..(10)
<220> FEATURE:
<221> NAME/KEY: 2'-OMe
<222> LOCATION: (16)..(16)

<400> SEQUENCE: 44
cuacgccauc agcuccaact t                                              21

<210> SEQ ID NO 45
<211> LENGTH: 21
<212> TYPE: DNA
<213> ORGANISM: Artificial Sequence
<220> FEATURE:
<223> OTHER INFORMATION: siRNA sequence
<220> FEATURE:
<221> NAME/KEY: RNA
<222> LOCATION: (1)..(19)
<220> FEATURE:
<221> NAME/KEY: 2'-OMe
<222> LOCATION: (3)..(4)
<220> FEATURE:
<221> NAME/KEY: 2'-OMe
<222> LOCATION: (9)..(10)
<220> FEATURE:
<221> NAME/KEY: 2'-OMe
<222> LOCATION: (12)..(13)
<220> FEATURE:
<221> NAME/KEY: 2'-OMe
<222> LOCATION: (17)..(18)
<220> FEATURE:
<221> NAME/KEY: DNA
<222> LOCATION: (20)..(21)

<400> SEQUENCE: 45
guuggagcug auggcguagt t                                              21
```

```
<210> SEQ ID NO 46
<211> LENGTH: 21
<212> TYPE: DNA
<213> ORGANISM: Artificial Sequence
<220> FEATURE:
<223> OTHER INFORMATION: siRNA sequence
<220> FEATURE:
<221> NAME/KEY: RNA
<222> LOCATION: (1)..(19)
<220> FEATURE:
<221> NAME/KEY: 2'-OMe
<222> LOCATION: (2)..(2)
<220> FEATURE:
<221> NAME/KEY: 2'-OMe
<222> LOCATION: (7)..(7)
<220> FEATURE:
<221> NAME/KEY: 2'-OMe
<222> LOCATION: (10)..(10)
<220> FEATURE:
<221> NAME/KEY: 2'-OMe
<222> LOCATION: (16)..(16)
<220> FEATURE:
<221> NAME/KEY: DNA
<222> LOCATION: (20)..(21)

<400> SEQUENCE: 46
cuacgccauc agcuccaact t                                             21

<210> SEQ ID NO 47
<211> LENGTH: 21
<212> TYPE: DNA
<213> ORGANISM: Artificial Sequence
<220> FEATURE:
<223> OTHER INFORMATION: siRNA sequence
<220> FEATURE:
<221> NAME/KEY: RNA
<222> LOCATION: (1)..(19)
<220> FEATURE:
<221> NAME/KEY: 2'-OMe
<222> LOCATION: (3)..(4)
<220> FEATURE:
<221> NAME/KEY: 2'-OMe
<222> LOCATION: (9)..(10)
<220> FEATURE:
<221> NAME/KEY: 2'-OMe
<222> LOCATION: (12)..(13)
<220> FEATURE:
<221> NAME/KEY: 2'-OMe
<222> LOCATION: (17)..(18)
<220> FEATURE:
<221> NAME/KEY: DNA
<222> LOCATION: (20)..(21)

<400> SEQUENCE: 47
guuggagcug auggcguagt t                                             21

<210> SEQ ID NO 48
<211> LENGTH: 21
<212> TYPE: DNA
<213> ORGANISM: Artificial Sequence
<220> FEATURE:
<223> OTHER INFORMATION: siRNA sequence
<220> FEATURE:
<221> NAME/KEY: RNA
<222> LOCATION: (1)..(19)
<220> FEATURE:
<221> NAME/KEY: DNA
<222> LOCATION: (20)..(21)

<400> SEQUENCE: 48
cuacgccauc agcuccaact t                                             21

<210> SEQ ID NO 49
```

-continued

```
<211> LENGTH: 21
<212> TYPE: DNA
<213> ORGANISM: Artificial Sequence
<220> FEATURE:
<223> OTHER INFORMATION: siRNA sequence
<220> FEATURE:
<221> NAME/KEY: RNA
<222> LOCATION: (1)..(19)
<220> FEATURE:
<221> NAME/KEY: 2'-OMe
<222> LOCATION: (3)..(4)
<220> FEATURE:
<221> NAME/KEY: 2'-OMe
<222> LOCATION: (17)..(18)
<220> FEATURE:
<221> NAME/KEY: DNA
<222> LOCATION: (20)..(21)

<400> SEQUENCE: 49
guuggagcug auggcguagt t                                              21

<210> SEQ ID NO 50
<211> LENGTH: 21
<212> TYPE: DNA
<213> ORGANISM: Artificial Sequence
<220> FEATURE:
<223> OTHER INFORMATION: siRNA sequence
<220> FEATURE:
<221> NAME/KEY: RNA
<222> LOCATION: (1)..(19)
<220> FEATURE:
<221> NAME/KEY: 2'-OMe
<222> LOCATION: (3)..(3)
<220> FEATURE:
<221> NAME/KEY: 2'-OMe
<222> LOCATION: (18)..(19)
<220> FEATURE:
<221> NAME/KEY: DNA
<222> LOCATION: (20)..(21)

<400> SEQUENCE: 50
cuacgccauc agcuccaact t                                              21

<210> SEQ ID NO 51
<211> LENGTH: 21
<212> TYPE: DNA
<213> ORGANISM: Artificial Sequence
<220> FEATURE:
<223> OTHER INFORMATION: siRNA sequence
<220> FEATURE:
<221> NAME/KEY: RNA
<222> LOCATION: (1)..(19)
<220> FEATURE:
<221> NAME/KEY: 2'-OMe
<222> LOCATION: (3)..(4)
<220> FEATURE:
<221> NAME/KEY: 2'-OMe
<222> LOCATION: (13)..(13)
<220> FEATURE:
<221> NAME/KEY: 2'-OMe
<222> LOCATION: (17)..(18)
<220> FEATURE:
<221> NAME/KEY: DNA
<222> LOCATION: (20)..(21)

<400> SEQUENCE: 51
guuggagcug auggcguagt t                                              21

<210> SEQ ID NO 52
<211> LENGTH: 21
<212> TYPE: DNA
<213> ORGANISM: Artificial Sequence
<220> FEATURE:
```

```
<223> OTHER INFORMATION: siRNA sequence
<220> FEATURE:
<221> NAME/KEY: RNA
<222> LOCATION: (1)..(19)
<220> FEATURE:
<221> NAME/KEY: 2'-OMe
<222> LOCATION: (3)..(3)
<220> FEATURE:
<221> NAME/KEY: 2'-OMe
<222> LOCATION: (7)..(7)
<220> FEATURE:
<221> NAME/KEY: 2'-OMe
<222> LOCATION: (18)..(19)
<220> FEATURE:
<221> NAME/KEY: DNA
<222> LOCATION: (20)..(21)

<400> SEQUENCE: 52
cuacgccauc agcuccaact t                                          21

<210> SEQ ID NO 53
<211> LENGTH: 21
<212> TYPE: DNA
<213> ORGANISM: Artificial Sequence
<220> FEATURE:
<223> OTHER INFORMATION: siRNA sequence
<220> FEATURE:
<221> NAME/KEY: RNA
<222> LOCATION: (1)..(19)
<220> FEATURE:
<221> NAME/KEY: 2'-OMe
<222> LOCATION: (2)..(4)
<220> FEATURE:
<221> NAME/KEY: 2'-OMe
<222> LOCATION: (9)..(10)
<220> FEATURE:
<221> NAME/KEY: 2'-OMe
<222> LOCATION: (12)..(13)
<220> FEATURE:
<221> NAME/KEY: 2'-OMe
<222> LOCATION: (17)..(18)
<220> FEATURE:
<221> NAME/KEY: DNA
<222> LOCATION: (20)..(21)

<400> SEQUENCE: 53
guuggagcug auggcguagt t                                          21

<210> SEQ ID NO 54
<211> LENGTH: 21
<212> TYPE: DNA
<213> ORGANISM: Artificial Sequence
<220> FEATURE:
<223> OTHER INFORMATION: siRNA sequence
<220> FEATURE:
<221> NAME/KEY: RNA
<222> LOCATION: (1)..(19)
<220> FEATURE:
<221> NAME/KEY: DNA
<222> LOCATION: (20)..(21)

<400> SEQUENCE: 54
cuacgccauc agcuccaact t                                          21

<210> SEQ ID NO 55
<211> LENGTH: 21
<212> TYPE: DNA
<213> ORGANISM: Artificial Sequence
<220> FEATURE:
<223> OTHER INFORMATION: siRNA sequence
<220> FEATURE:
<221> NAME/KEY: 2'-OMe
<222> LOCATION: (1)..(1)
```

```
<220> FEATURE:
<221> NAME/KEY: RNA
<222> LOCATION: (1)..(19)
<220> FEATURE:
<221> NAME/KEY: 2'-OMe
<222> LOCATION: (3)..(3)
<220> FEATURE:
<221> NAME/KEY: 2'-OMe
<222> LOCATION: (5)..(5)
<220> FEATURE:
<221> NAME/KEY: 2'-OMe
<222> LOCATION: (7)..(7)
<220> FEATURE:
<221> NAME/KEY: 2'-OMe
<222> LOCATION: (9)..(9)
<220> FEATURE:
<221> NAME/KEY: 2'-OMe
<222> LOCATION: (11)..(11)
<220> FEATURE:
<221> NAME/KEY: 2'-OMe
<222> LOCATION: (13)..(13)
<220> FEATURE:
<221> NAME/KEY: 2'-OMe
<222> LOCATION: (15)..(15)
<220> FEATURE:
<221> NAME/KEY: 2'-OMe
<222> LOCATION: (17)..(17)
<220> FEATURE:
<221> NAME/KEY: 2'-OMe
<222> LOCATION: (19)..(19)
<220> FEATURE:
<221> NAME/KEY: DNA
<222> LOCATION: (20)..(21)

<400> SEQUENCE: 55
guuggagcug auggcguagt t                                          21

<210> SEQ ID NO 56
<211> LENGTH: 21
<212> TYPE: DNA
<213> ORGANISM: Artificial Sequence
<220> FEATURE:
<223> OTHER INFORMATION: siRNA sequence
<220> FEATURE:
<221> NAME/KEY: RNA
<222> LOCATION: (1)..(19)
<220> FEATURE:
<221> NAME/KEY: 2'-OMe
<222> LOCATION: (2)..(2)
<220> FEATURE:
<221> NAME/KEY: 2'-OMe
<222> LOCATION: (4)..(4)
<220> FEATURE:
<221> NAME/KEY: 2'-OMe
<222> LOCATION: (6)..(6)
<220> FEATURE:
<221> NAME/KEY: 2'-OMe
<222> LOCATION: (8)..(8)
<220> FEATURE:
<221> NAME/KEY: 2'-OMe
<222> LOCATION: (14)..(14)
<220> FEATURE:
<221> NAME/KEY: 2'-OMe
<222> LOCATION: (16)..(16)
<220> FEATURE:
<221> NAME/KEY: 2'-OMe
<222> LOCATION: (18)..(18)
<220> FEATURE:
<221> NAME/KEY: DNA
<222> LOCATION: (20)..(21)

<400> SEQUENCE: 56
cuacgccauc agcuccaact t                                          21

<210> SEQ ID NO 57
```

```
<211> LENGTH: 19
<212> TYPE: RNA
<213> ORGANISM: Artificial Sequence
<220> FEATURE:
<223> OTHER INFORMATION: siRNA sequence
<220> FEATURE:
<221> NAME/KEY: 2'-OMe
<222> LOCATION: (1)..(1)
<220> FEATURE:
<221> NAME/KEY: 2'-OMe
<222> LOCATION: (3)..(3)
<220> FEATURE:
<221> NAME/KEY: 2'-OMe
<222> LOCATION: (5)..(5)
<220> FEATURE:
<221> NAME/KEY: 2'-OMe
<222> LOCATION: (7)..(7)
<220> FEATURE:
<221> NAME/KEY: 2'-OMe
<222> LOCATION: (9)..(9)
<220> FEATURE:
<221> NAME/KEY: 2'-OMe
<222> LOCATION: (11)..(11)
<220> FEATURE:
<221> NAME/KEY: 2'-OMe
<222> LOCATION: (13)..(13)
<220> FEATURE:
<221> NAME/KEY: 2'-OMe
<222> LOCATION: (15)..(15)
<220> FEATURE:
<221> NAME/KEY: 2'-OMe
<222> LOCATION: (17)..(17)
<220> FEATURE:
<221> NAME/KEY: 2'-OMe
<222> LOCATION: (19)..(19)

<400> SEQUENCE: 57
guuggagcug auggcguag                                              19

<210> SEQ ID NO 58
<211> LENGTH: 19
<212> TYPE: RNA
<213> ORGANISM: Artificial Sequence
<220> FEATURE:
<223> OTHER INFORMATION: siRNA sequence
<220> FEATURE:
<221> NAME/KEY: 2'-OMe
<222> LOCATION: (2)..(2)
<220> FEATURE:
<221> NAME/KEY: 2'-OMe
<222> LOCATION: (4)..(4)
<220> FEATURE:
<221> NAME/KEY: 2'-OMe
<222> LOCATION: (6)..(6)
<220> FEATURE:
<221> NAME/KEY: 2'-OMe
<222> LOCATION: (8)..(8)
<220> FEATURE:
<221> NAME/KEY: 2'-OMe
<222> LOCATION: (14)..(14)
<220> FEATURE:
<221> NAME/KEY: 2'-OMe
<222> LOCATION: (16)..(16)
<220> FEATURE:
<221> NAME/KEY: 2'-OMe
<222> LOCATION: (18)..(18)

<400> SEQUENCE: 58
cuacgccauc agcuccaac                                              19

<210> SEQ ID NO 59
<211> LENGTH: 19
<212> TYPE: RNA
<213> ORGANISM: Artificial Sequence
<220> FEATURE:
```

```
<223> OTHER INFORMATION: siRNA sequence
<220> FEATURE:
<221> NAME/KEY: 2'-OMe
<222> LOCATION: (2)..(4)
<220> FEATURE:
<221> NAME/KEY: 2'-OMe
<222> LOCATION: (9)..(13)
<220> FEATURE:
<221> NAME/KEY: 2'-OMe
<222> LOCATION: (17)..(18)

<400> SEQUENCE: 59
guuggagcug auggcguag                                                    19

<210> SEQ ID NO 60
<211> LENGTH: 19
<212> TYPE: RNA
<213> ORGANISM: Artificial Sequence
<220> FEATURE:
<223> OTHER INFORMATION: siRNA sequence

<400> SEQUENCE: 60
cuacgccauc agcuccaac                                                    19

<210> SEQ ID NO 61
<211> LENGTH: 19
<212> TYPE: RNA
<213> ORGANISM: Artificial Sequence
<220> FEATURE:
<223> OTHER INFORMATION: siRNA sequence
<220> FEATURE:
<221> NAME/KEY: 2'-OMe
<222> LOCATION: (2)..(4)
<220> FEATURE:
<221> NAME/KEY: 2'-OMe
<222> LOCATION: (9)..(13)

<400> SEQUENCE: 61
guuggagcug auggcguag                                                    19

<210> SEQ ID NO 62
<211> LENGTH: 19
<212> TYPE: RNA
<213> ORGANISM: Artificial Sequence
<220> FEATURE:
<223> OTHER INFORMATION: siRNA sequence

<400> SEQUENCE: 62
cuacgccauc agcuccaac                                                    19

<210> SEQ ID NO 63
<211> LENGTH: 19
<212> TYPE: RNA
<213> ORGANISM: Artificial Sequence
<220> FEATURE:
<223> OTHER INFORMATION: siRNA sequence
<220> FEATURE:
<221> NAME/KEY: 2'-OMe
<222> LOCATION: (1)..(4)
<220> FEATURE:
<221> NAME/KEY: 2'-OMe
<222> LOCATION: (9)..(13)
<220> FEATURE:
<221> NAME/KEY: 2'-OMe
<222> LOCATION: (19)..(19)

<400> SEQUENCE: 63
guuggagcug auggcguag                                                    19
```

```
<210> SEQ ID NO 64
<211> LENGTH: 19
<212> TYPE: RNA
<213> ORGANISM: Artificial Sequence
<220> FEATURE:
<223> OTHER INFORMATION: siRNA sequence

<400> SEQUENCE: 64
cuacgccauc agcuccaac                                                  19

<210> SEQ ID NO 65
<211> LENGTH: 19
<212> TYPE: RNA
<213> ORGANISM: Artificial Sequence
<220> FEATURE:
<223> OTHER INFORMATION: siRNA sequence
<220> FEATURE:
<221> NAME/KEY: 2'-OMe
<222> LOCATION: (1)..(3)
<220> FEATURE:
<221> NAME/KEY: 2'-OMe
<222> LOCATION: (9)..(13)
<220> FEATURE:
<221> NAME/KEY: 2'-OMe
<222> LOCATION: (17)..(19)

<400> SEQUENCE: 65
guuggagcug auggcguag                                                  19

<210> SEQ ID NO 66
<211> LENGTH: 19
<212> TYPE: RNA
<213> ORGANISM: Artificial Sequence
<220> FEATURE:
<223> OTHER INFORMATION: siRNA sequence
<220> FEATURE:
<221> NAME/KEY: 2'-OMe
<222> LOCATION: (4)..(6)
<220> FEATURE:
<221> NAME/KEY: 2'-OMe
<222> LOCATION: (14)..(16)

<400> SEQUENCE: 66
cuacgccauc agcuccaac                                                  19

<210> SEQ ID NO 67
<211> LENGTH: 19
<212> TYPE: RNA
<213> ORGANISM: Artificial Sequence
<220> FEATURE:
<223> OTHER INFORMATION: siRNA sequence
<220> FEATURE:
<221> NAME/KEY: 2'-OMe
<222> LOCATION: (2)..(4)
<220> FEATURE:
<221> NAME/KEY: 2'-OMe
<222> LOCATION: (9)..(10)
<220> FEATURE:
<221> NAME/KEY: 2'-OMe
<222> LOCATION: (12)..(13)
<220> FEATURE:
<221> NAME/KEY: 2'-OMe
<222> LOCATION: (17)..(18)

<400> SEQUENCE: 67
guuggagcug auggcguag                                                  19

<210> SEQ ID NO 68
<211> LENGTH: 19
<212> TYPE: RNA
<213> ORGANISM: Artificial Sequence
```

```
<220> FEATURE:
<223> OTHER INFORMATION: siRNA sequence
<220> FEATURE:
<221> NAME/KEY: 2'-OMe
<222> LOCATION: (2)..(2)
<220> FEATURE:
<221> NAME/KEY: 2'-OMe
<222> LOCATION: (7)..(7)
<220> FEATURE:
<221> NAME/KEY: 2'-OMe
<222> LOCATION: (16)..(16)

<400> SEQUENCE: 68
cuacgccauc agcuccaac                                              19
```

METHODS AND COMPOSITIONS FOR RNAI-BASED CANCER TREATMENT

CROSS REFERENCE TO RELATED APPLICATIONS

This is a divisional of U.S. patent application Ser. No. 13/451,231, filed on Apr. 19, 2012.

FIELD OF THE INVENTION

The present invention generally concerns methods and compositions for treating mutated K-ras expressing cancers.

BACKGROUND OF THE INVENTION

K-ras is a GTPase protein encoded by the Kirsten rat sarcoma 2 viral oncogene homolog (K-ras) oncogene (also known as K-ras2 or RASK2; PubMed Gene ID # 3845), which belongs to the family of RAS proteins.

The human RAS family consists of three closely related proto-oncogenes: c-Harvey (H)-RAS, c-Kirsten (K)-RAS, and N-RAS, which share 90% of their peptide sequence. RAS proteins are localized in the inner cell membrane, bind GDP and GTP, and possess an intrinsic GTPase activity, implicated in the regulation of their activity. RAS proteins influence proliferation, differentiation, transformation, and apoptosis by relaying mitogenic and growth signals into the cytoplasm and the nucleolus. In a normal cell, most of the RAS molecules are present in an inactive GDP-bound conformation.

K-ras Mutations

Genetic alterations in the K-ras signaling pathway are involved in more than 90% of cases of Pancreatic Cancer (PC) (Réjiba et al, and references cited therein); the majority of such mutations are gain-of-function mutations at codon 12 (K-rasG12D). PC is an aggressive disease, being one of the leading causes of cancer-related death in the western world. Mutations in K-ras are also well known in other cancers. For example, K-ras is involved in the development and progression of colorectal cancer (CRC). Mutations are present in about 40% of CRC cases, most commonly at codons 12 and 13. These mutations prevent dephosphorylation and inactivation of the protein, causing it to be permanently switched on, independently of EGFR-mediated signaling. These mutated K-ras proteins are unlikely be affected by inhibition of EGFR, since the mutation causes the encoded K-ras protein to "freeze" in its active state for a much longer duration than its non-mutated counterpart. Hence, the response to anti-EGFR mABs is strongly reduced in tumors with mutated K-ras (Normanno et al). K-ras mutations also occur in 20-30% of lung cancer patients.

Anti-K-ras Mutations RNAi-based Treatment:

RNAi vectors (Brummelkamp et al) and siRNA against mutated K-ras can lead to apoptosis of cancer cells in vitro and in vivo in mice and reduce tumor growth (Wang et al, Morioka et al, Fleming et al, Réjiba et al, WO2010/001325). Moreover, anti mutated K-ras treatment potentially can slow the epithelial-to-mesenchymal transition (EMT) and thereby slow metastasis of PC disease. For example Singh et al observed an association between epithelial differentiation and tumor cell viability, and that EMT regulators in "K-Ras-addicted" cancers represent candidate therapeutic targets. siRNA (short interfering RNA) have been delivered by millimeter-scale depot technology against mutated K-ras (WO2010/001325 to Shemi) and other non-oncology targets (US2008/0124370 to Marx).

SUMMARY OF THE INVENTION

The present invention relates to methods and compositions for prolonged intratumoral release of RNAi agents that specifically target mutated K-ras. Specifically, in accordance with certain aspects of the present invention, the present inventors have discovered that anti-K-rasG12D RNAi agents having particular sequences and conformations are able to achieve high anti-tumor efficacy in the context of controlled-release drug delivery devices of the present invention.

In accordance with other aspects of the present invention, the present inventors have discovered that certain modifications to anti-K-rasG12D RNAi agents confer improved efficacy thereto.

In accordance with yet other aspects of the present invention, the present inventors have discovered anti-K-rasG12D-containing drug delivery devices exhibit particular efficacy in combination with anti-cancer agents, as described herein.

As used herein "comprising" is to be interpreted as specifying the presence of the stated features, integers, steps, or components as referred to, but does not preclude the presence or addition of one or more features, integers, steps, or components, or groups thereof. Thus, for example, a drug delivery device comprising a biocompatible and biodegradable polymeric matrix and a given anti-K-rasG12D RNAi agent may contain additional excipients or components, such as non-polymeric components, non-matrix components, and additional agents. Additionally, the term "comprising" is intended to include, as separate embodiments, embodiments encompassed by the terms "consisting essentially of" and "consisting of." The phrase "consisting essentially of" limits the scope of a claim to the recited materials or steps, either alone or in combination with additional materials or steps that do not materially affect the basic and novel characteristics of the claimed invention.

In light of the disclosure provided herein, it will be appreciated by those skilled in the art, in light of the present disclosure, that methods of the present invention are suitable for treating any type of solid tumor expressing a mutated K-ras protein.

BRIEF DESCRIPTION OF THE DRAWINGS

The following figures are by way of illustrative example and are not meant to be taken as limiting the claimed invention.

FIG. 6. Summary of stability and efficacy data with various OMe-modified-siG12D measured at 24h, 1w, 2w and 4w (stability), and after 120h (efficacy).

DETAILED DESCRIPTION OF THE EMBODIMENTS

Figure 1A:
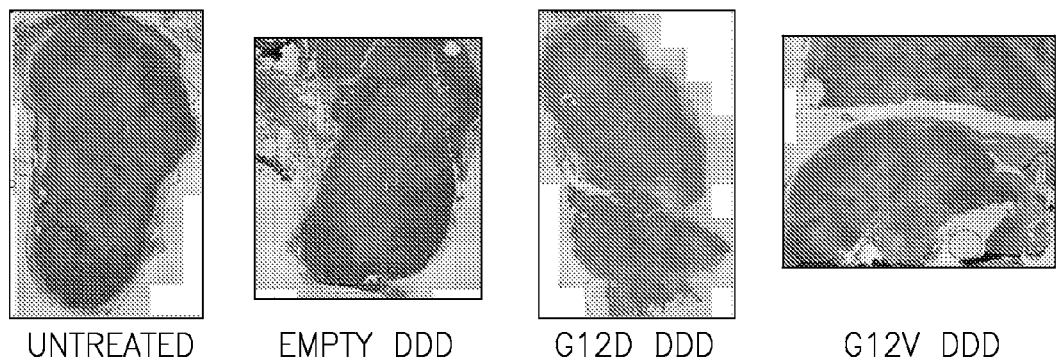
FIG. 1. A. Representative slides depicting CDC47 immuno-staining of subcutaneous Capan-1 tumors (which express G12V-mutated K-ras) from the following treatment groups: Untreated, Empty DDD ("Empty L"), siG12D-DDD ("2G12DL"), siG12V-DDD ("2G12VL"). White-gray areas represent necrosis, and pink-purple areas represent living cells. B. Computer count of dividing cells in stained area. An asterisk indicates a P-value of <0.05 of the ratio of necrotic/peripheral area, relative to untreated, by Student's T-test.

In one embodiment, the present invention provides a millimeter-scale drug delivery device (DDD) comprising:

A. A biodegradable matrix; and

B. An RNAi (RNA interference) agent incorporated within the biodegradable matrix, wherein the RNAi agent comprises a duplex region, and the nucleotide sequence of the duplex region of the sense strand consists of

```
a sequence selected from SEQ ID No: 1-7, namely
                                              (SEQ ID No: 1)
GUUGGAGCUGAUGGCG, (SEQ ID No: 2)
GUUGGAGCUGUUGGCG, (SEQ ID No: 3)
GUUGGAGCUGCUGGCG, (SEQ ID No: 4)
GUUGGAGCUAGUGGCG, (SEQ ID No: 5)
GUUGGAGCUUGUGGCG, (SEQ ID No: 6)
GUUGGAGCUGGUGACG,
and (SEQ ID No: 7)
GUUGGAGCUGGUUGCG,
either alone or followed by:

a sequence selected from: (i)
                                              (SEQ ID No: 8)
UAGGCAAGAGUGCC
and
```

(b) a 5'-fragment of 1-13 nucleotides inclusive of SEQ ID No: 8. "Followed by" in this regard means that the 3'-terminus of the sequence selected from SEQ ID No: 1-7 is connected to the 5'-terminus of SEQ ID No: 8 or a fragment thereof.

For purposes of illustration, the following sense strands contain SEQ ID No: 1 and all or a portion of SEQ ID No: 8: GUUGGAGCUGAUGGCGU (SEQ ID No: 16), GUUGGAGCUGAUGGCGUA (SEQ ID No: 17), GUUGGAGCUGAUGGCGUAG (SEQ ID No: 18), GUUGGAGCUGAUGGCGUAGG (SEQ ID No: 19), GUUGGAGCUGAUGGCGUAGGC (SEQ ID No: 20), GUUGGAGCUGAUGGCGUAGGCA (SEQ ID No: 21), GUUGGAGCUGAUGGCGUAGGCAA (SEQ ID No: 22), GUUGGAGCUGAUGGCGUAGGCAAG (SEQ ID No: 23), GUUGGAGCUGAUGGCGUAGGCAAGA (SEQ ID No: 24), GUUGGAGCUGAUGGCGUAGGCAAGAG (SEQ ID No: 25), GUUGGAGCUGAUGGCGUAGGCAAGAGU (SEQ ID No: 26), GUUGGAGCUGAUGGCGUAGGCAAGAGUG (SEQ ID No: 27), GUUGGAGCUGAUGGCGUAGGCAAGAGUGC (SEQ ID No: 28), and GUUGGAGCUGAUGGCGUAGGCAAGAGUGCC (SEQ ID No: 29) Similar sense strains may be readily derived from each of SEQ ID No: 2-7 together with all or a portion of SEQ ID No: 8.

In certain embodiments, the aforementioned 5' fragment of SEQ ID No: 8 is at least 3 nucleotides in length; thus, the duplex region of the antisense nucleotide is at least 19 nucleotides in length.

In other embodiments, the duplex region is 19 nucleotides in length (thus comprising both one of SEQ ID No: 1-7 with a 3-nucleotide fragment of SEQ ID No: 8). More specific embodiments of such sequences are those selected from GUUGGAGCUGAUGGCGUAG (SEQ ID No: 9), GUUGGAGCUGUUGGCGUAG (SEQ ID No: 10), GUUGGAGCUGCUGGCGUAG (SEQ ID No: 11), GUUGGAGCUAGUGGCGUAG (SEQ ID No: 12), GUUGGAGCUUGUGGCGUAG (SEQ ID No: 13), and GUUGGAGCUGGUGACGUAG (SEQ ID No: 14), and GUUGGAGCUGGUUGCGUAG (SEQ ID No: 15).

In other embodiments, the duplex region is 16 nucleotides in length (thus consisting of one of SEQ ID No: 1-7 alone). In other embodiments, the duplex region is 17, 18, 20, 21, 22, 23, 24, 25, 26, 27, 28, or 29 nucleotides in length (thus comprising one of SEQ ID No: 1-7, together with a fragment of SEQ ID No: 8 that is 1, 2, 4, 5, 6, 7, 8, 9, 10, 11, 12, or 13 nucleotides, respectively). In other embodiments, the duplex region is 30 nucleotides in length (thus comprising one of SEQ ID No: 1-7, together with SEQ ID No: 8 in its entirety).

Reference herein to the "duplex region of the sense strand" indicates the portion of the sense strand that exists in a duplex structure after hybridization to the antisense strand Similarly, reference to the "duplex region of the antisense strand" indicates the portion of the antisense strand that exists in a duplex structure after hybridization to the sense strand. In various embodiments, the duplex region of the sense strand may be either the entire sense strand or a fragment thereof. Similarly, the duplex region of the antisense strand may be either the entire antisense strand or a fragment thereof.

In certain preferred embodiments, the duplex region is perfectly complementary. Thus, the duplex region of the antisense strand is complementary to the duplex region of the sense strand. For purposes of illustration, the following antisense strands have a sequence perfectly complementary to SEQ ID No: 1-7, respectively: CGCCAUCAGCUCCAAC (SEQ ID No: 30), CGCCAACAGCUCCAAC (SEQ ID No: 31), CGCCAGCAGCUCCAAC (SEQ ID No: 32), CGCCACUAGCUCCAAC (SEQ ID No: 33), CGCCACAAGCUCCAAC (SEQ ID No: 34), CGUCACCAGCUCCAAC (SEQ ID No: 35), and CGCAACCAGCUCCAAC (SEQ ID No: 36).

Reference herein to the "nucleotide sequence of the duplex region" relates to the sequence of the nucleotides found in the duplex region. For these purposes, modified ribonucleotides are considered to have the same identity as the ribonucleotide from which they were derived (the "parent ribonucleotide"), provided that they retain the base pairing specificity of the parent ribonucleotide. Thus, cytosine containing a 2'-OMe modification, for example, is still considered cytosine, since it retains the ability to pair with guanine.

In still other embodiments, a DDD of the present invention comprises more than one, for example 2, 3, 4, or 5, of the 16-30 nucleotide RNAi agents described herein, in other words, RNAi agents whose sense strand comprises (a) a sequence selected from SEQ ID No: 1-7, optionally in combination with (b) either SEQ ID No: 8 or a 1-13 nucleotide fragment thereof. In even more specific embodiments, a DDD of the present invention comprises more than one, for example 2, 3, 4, or 5, of the 19 nucleotide RNAi agents described herein, in other words, RNAi agents whose sense strand consists a sequence selected from SEQ ID No: 9-15.

In still other embodiments, at least one of the sense strand and the antisense strand further comprises a 3'-overhang 1-6 nucleotides (nt) in length, in other words, a region that does not hybridize with the other strand. In more specific embodiments, the 1-6-nt 3'-overhang is present on both the sense strand and the antisense strand.

In other embodiments, the overhang present on at least one of the sense strand and the antisense strand is a 2-nt 3'-overhang. In still more specific embodiments, the overhangs present both the sense strand and the antisense strand are 2-nt 3'-overhangs.

In other embodiments, the 3'-overhang present on at least one of the sense strand and the antisense strand consists of dTdT (a dimer of deoxythymidine). In still more specific embodiments, 3'-overhangs are present on both the sense strand and the antisense strand, each of which consists of dTdT.

In certain embodiments, the sense and antisense strands of an RNAi agent of methods and compositions of the present invention each contain only cytosine, guanine, adenine, and thymidine in the duplex region and the dTdT overhangs.

Suitable Nucleotides and Nucleotide Analogues

The term "nucleotide" as used herein refers to RNA nucleotides cytosine, guanine, adenine, and thymidine and to other similar nucleotide analogues suitable for use in RNAi agents. Such nucleotide analogues may generally be used as the building blocks of the RNAi agents described herein, except where indicated otherwise. Except where stated explicitly, nothing in this application is intended to preclude the utilization of non-classical nucleotide analogues, for example nucleotide analogues whose base or backbone has been chemically modified to enhance its stability or usefulness as an RNAi agent, provided that they pair with the appropriate complementary bases, as previously mentioned. In certain embodiments, nucleotide analogues that may be used in methods and compositions of the present invention include derivatives wherein the sugar is modified, as in 2'-O-methyl, 2'-O-allyl, 2'-deoxy-2'-fluoro, and 2',3'-dideoxynucleoside derivatives;

nucleic acid analogs based on other sugar backbones, such as threose; locked nucleic acid derivatives; bicyclo sugars; hexose, glycerol and glycol sugars; nucleic acid analogs based on non-ionic backbones, such as "peptide nucleic acids", these nucleic acids and their analogs in non-linear topologies, including as dendrimers, comb-structures, and nanostructures, and these nucleic acids and their analogs carrying tags (e.g., fluorescent, functionalized, or binding) to the ends, sugars, or nucleobases.

One non-limiting example of non-classical nucleotide analogues suitable for use in methods and compositions in accordance with the present invention include locked nucleic acid (LNA) nucleotide analogues. Certain embodiments of LNA nucleotide analogues are bicyclic nucleic acid analogs that contain one or more 2'-O, 4'-C methylene linkages, which effectively lock the furanose ring in a C3'-endo conformation. This methylene linkage "bridge" restricts the flexibility of the ribofuranose ring and locks the structure into a rigid bicyclic formation. Because of its unique structural conformation, oligonucleotides comprising LNA nucleotide analogues demonstrate a much greater affinity and specificity to their complementary nucleic acids than do natural DNA counterparts. LNAs typically hybridize to complementary nucleic acids even under adverse conditions, such as under low salt concentrations. LNA nucleotide analogues are commercially available, and are described, inter alia, in U.S. Pat. Nos. 6,130,038, 6,268,490, and 6,670,461.

Another non-limiting example of non-classical nucleotide analogues suitable for use in methods and compositions in accordance with the present invention are peptide nucleic acid (PNA) nucleotide analogues. In certain embodiments of PNA nucleotide analogues, the negatively charged sugar-phosphate backbone of DNA is replaced by a neutral polyamide backbone composed of N-(2-aminoethyl) glycine units, such as in the illustrative example below, wherein B represents a nucleoside base. The chemical configuration of PNA typically enables the nucleotide bases to be positioned in approximately the same place as in natural DNA, allowing PNA to hybridize with complementary DNA or RNA sequence. PNA nucleotide analogues are commercially available, and are described, inter alia, in the PCT Applications having the Publication Nos. WO 92/20702, WO 92/20703 and WO 93/12129.

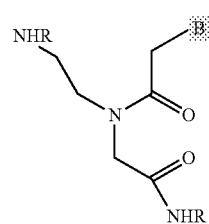

Another non-limiting example of non-classical nucleotide analogues suitable for use in methods and compositions of the present invention are glycol nucleic acid (GNA) nucleotide analogues (Zhang, L et al (2005) "A simple glycol nucleic acid". J. Am. Chem. Soc. 127:4174-4175). Certain embodiments of GNA nucleotide analogues have an acyclic propylene glycol phosphodiester backbone and have one of the structures below, wherein B represents a nucleoside base:

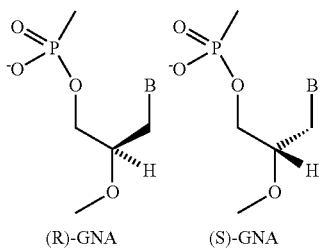

(R)-GNA      (S)-GNA

Another non-limiting example of non-classical nucleotide analogues suitable for use in methods and compositions of the present invention are threose nucleic acid (TNA) described in Wu et al, "Nucleotide Analogues" Organic Letters, 2002, 4(8):1279-1282. Certain embodiments of TNA nucleotide analogues have the structure below, wherein B represents a nucleoside base:

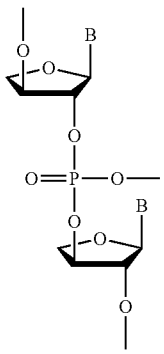

Another non-limiting example of non-classical nucleotide analogues suitable for use in methods and compositions in accordance with aspects of the present invention are bicyclic and tricyclic nucleoside analogs (Steffens et al, Hely Chim Acta (1997) 80:2426-2439; Steffens et al, J Am Chem Soc (1999) 121: 3249-3255; Renneberg et al, J Am Chem Soc (2002) 124: 5993-6002; and Renneberg et al, Nucl Acids Res (2002) 30: 2751-2757).

Another non-limiting example of non-classical nucleotide analogues suitable for use in methods and compositions of the present invention are phosphonomonoester nucleic acids which incorporate a phosphorus group in the backbone, for example analogues with phosphonoacetate and thiophosphonoacetate internucleoside linkages (U.S. patent application Ser. No. 2005/0106598; Sheehan et al, Nucleic Acids Res (2003); 31(14):4109-18). In other embodiments, a cyclobutyl ring replaces the naturally occurring furanosyl ring.

In other embodiments of non-classical nucleotide analogues suitable for use in methods and compositions of the present invention, the base is modified. A representative, non-limiting list of modified nucleobases includes 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl

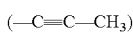

uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-b)(1,4)benzoxazin-2(3H)-one), carbazole cytidine (2H-pyrimido(4,5-b)indol-2-one), and pyridoindole cytidine (H-pyrido(3',2':4,5)pyrrolo(2,3-d)pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808; those disclosed in The Concise Encyclopedia Of Polymer Science And Engineering, pages 858-859, Kroschwitz, J. I., ed. John Wiley & Sons, 1990; those disclosed by Englisch et al., Angewandte Chemie, International Edition, 1991, 30, 613; and those disclosed by Sanghvi, Y. S., Chapter 15, Antisense Research and Applications, pages 289-302, Crooke, S. T. and Lebleu, B., ed., CRC Press, 1993. Certain of these nucleobases are known to those skilled in the art as suitable for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. Modified nucleobases and their use are described, inter alia, in U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,681,941; and 5,750,692.

Another non-limiting example of non-classical nucleotide analogues suitable for use in methods and compositions of the present invention are polycyclic heterocyclic compounds in place of one or more of the naturally-occurring heterocyclic base moieties. A number of tricyclic heterocyclic compounds have been previously reported. Such compounds are routinely used in antisense applications to increase the binding properties of the modified strand to a target strand. The most studied modifications are targeted to guanosines hence they have been termed G-clamps or cytidine analogs. Representative cytosine analogs that make 3 hydrogen bonds with a guanosine in a second strand include 1,3-diazaphenoxazine-2-one (Kurchavov, et al., Nucleosides and Nucleotides, 1997, 16, 1837-1846), 1,3-diazaphenothiazine-2-one, (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one (Wang, J.; Lin, K.-Y., Matteucci, M. Tetrahedron Lett. 1998, 39, 8385-8388). Incorporated into oligonucleotides these base modifications were shown to hybridize with complementary guanine and the latter was also shown to hybridize with adenine and to enhance helical thermal stability by extended stacking interactions.

Other examples of non-classical nucleotide analogues suitable for use in methods and compositions of the present invention are described in US Application Publication No. 2003/0207804 and 2003/0175906.

In other embodiments, an RNAi agent used in methods and compositions of the present invention is conjugated to a cholesterol moiety.

In still other embodiments, an RNAi agent used in methods and compositions of the present invention is conjugated to an α-tocopherol moiety.

2'-OMe Modifications

In more specific embodiments, an RNAi agent used in methods and compositions of the present invention is chemically modified with a modification selected from 2'-OMe and 2'-O-methoxy on at least one residue of at least one strand thereof. In other, more specific embodiments, the RNAi agent is chemically modified with 2'-OMe or 2'-O-methoxy on at least one residue of each of its 2 strands. In still more specific embodiments, the modification is 2'-OMe. In yet more specific embodiments, the 2'-OMe modification is present on at least one residue of each of its 2 strands.

In even more specific embodiments, four 2'-OMe modifications are present on each strand of the RNAi agent. Alternatively, four 2'-OMe modifications are present on one strand of the RNAi agent, while the other strand contains no modified bases (deoxyribonucleotides naturally occurring in DNA are not considered modified bases for these purposes). In still other embodiments, eight 2'-OMe modifications are present on one strand of the RNAi agent, while the other strand contains four 2'-OMe modifications.

In yet other embodiments, an RNAi agent used in methods and compositions of the present invention is chemically modified with 2'-F.

In more particular embodiments, the sequences of the sense and antisense strands of the RNAi agent of a DDD of methods and compositions of the present invention are:

```
                                         (SEQ ID No: 37)
5'-GUoUoGGAGCUGAUGGCGoUoAGdTdT
and (SEQ ID No: 38)
5'-CUACGCCAUCAGCUCCAACdTdT,
respectively.
```

As used herein, "o" preceding a residue denotes a 2'-O-Methyl modification of said residue.

Alternatively, the sequences of the sense and antisense strands of the RNAi agent are:

```
                                         (SEQ ID No: 39)
5'-GUoUGGAGCoUGAoUGGCGoUAG
and (SEQ ID No: 40)
5'-CoUACGCoCAUoCAGCUCoCAAC,
respectively.
```

Another aspect of the present invention provides an RNAi agent, wherein the sequences of the sense and antisense strands of the RNAi agent are:

```
                                         (SEQ ID No: 37)
5'-GUoUoGGAGCUGAUGGCGoUoAGdTdT
and (SEQ ID No: 38)
5'-CUACGCCAUCAGCUCCAACdTdT,
respectively.
```

Yet another aspect of the present invention provides an RNAi agent, wherein the sequences of the sense and antisense strands of the RNAi agent are:

```
                                         (SEQ ID No: 39)
5'-GUoUGGAGCoUGAoUGGCGoUAG
and (SEQ ID No: 40)
5'-CoUACGCoCAUoCAGCUCoCAAC,
respectively.
```

Another aspect of the present invention provides a pharmaceutical composition comprising one of the above RNAi agents.

Millimeter-scale Implant/Matrix Drug Delivery Devices

The drug delivery device of the present invention may be a cylinder, in other embodiments a sphere, and in other embodiments, another shape suitable for an implant.

In certain preferred embodiments, a biodegradable matrix used in methods and compositions of the present invention is a polymeric biodegradable matrix. "Polymeric" as used herein refers to the characteristic of comprising a polymer. In more specific embodiments, the biodegradable matrix is held together by the structure of the polymer.

In other embodiments, a biodegradable matrix used in methods and compositions of the present invention is a biocompatible biodegradable matrix. "Biocompatible" as used herein refers to the characteristic of not inducing toxic effects, either as a result of reactivity with the human immune system or body tissues, or the production of toxic degradation by-products. In more specific embodiments, the biodegradable matrix is a polymeric, biocompatible biodegradable matrix.

In yet other embodiments, a DDD of the present invention is biostable.

"Millimeter-scale", as used herein, refers to a device whose smallest diameter is at least 0.24 mm (fitting within the inner diameter of a 25-gauge needle). In certain preferred embodiments, each of the dimensions (diameter, in the case of a sphere or cylinder; and height and/or width or length, in the case of a cylinder, box-like structure, cube, or other shape with flat walls) is between 0.3-10 mm, inclusive. In more preferred embodiments, each dimension is between 0.5-8 mm, inclusive. In more preferred embodiments, each dimension is between 0.6-1.3 mm, inclusive.

In more preferred embodiments, the device is a cylinder, having a diameter of 0.1-2.5 mm, inclusive, more preferably 0.2-2.0 mm, more preferably 0.3-1.5 mm, more preferably 0.38-0.98 mm, more preferably 0.48-0.88 mm, more preferably 0.53-0.83 mm, more preferably 0.58-0.78 mm, more preferably 0.63-0.73 mm, more preferably 0.68 mm In other preferred embodiments, the cylinder has a length of 0.5-3.5 mm, inclusive, more preferably 0.7-3.0 mm, more preferably 0.9-2.5 mm, more preferably 1.0-2.0 mm, more preferably 1.1-1.5, more preferably 1.3 mm In other embodiments, the cylinder has a diameter of 0.38-0.98 mm, inclusive and a length of 0.5-3.5 mm, inclusive. In more preferred embodiments, the diameter is 0.48-0.88 mm, and the length is 0.7-3.0 mm In more preferred embodiments, the diameter is 0.53-0.83 mm, and the length is 0.9-2.5 mm In more preferred embodiments, the diameter is 0.58-0.78 mm, and the length is 1.0-2.0 mm In more preferred embodiments, the diameter is 0.63-0.73 mm, and the length is 1.1-1.5 mm In more preferred embodiments, the diameter is 0.68 mm, and the length is 1.3 mm In still other embodiments, the device is a suitable size for administration with a endoscope and a 19-gauge needle.

In other embodiments, the volume of the device is between 0.1 mm$^3$ and 1000 mm$^3$.

In other embodiments, the w/w agent:polymer load ratio above 1:100. In more preferred embodiments, the load is above 1:20. In more preferred embodiments, the load is above 1:9. In more preferred embodiments, the load is above 1:3

In other embodiments, the device is a technology described in US Patent Application Pub. No. 2011/0195123, the contents of which are incorporated herein by reference.

The DDD in some embodiments comprises degradable polymers, wherein the release mechanism includes both bulk erosion and diffusion; or in some embodiments, non degradable, or slowly degraded polymers are used, wherein the predominant release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). The term "constant" refers to a diffusion rate that is preferably maintained above the lower threshold of therapeutic effectiveness, but which may still optionally feature an initial burst and/or fluctuate, for example increasing and decreasing to a certain degree. In other embodiments, there is an initial burst of less than 10% of the total amount of drug, which may be considered negligible. In other embodiments, there is an initial burst of about 20% of the total amount of drug. In other embodiments, the design enables initial a strong burst of 30% or more of the total amount of drug. The diffusion rate is preferably so maintained for a prolonged period, and it can be considered constant to a certain level to optimize the therapeutically effective period, for example the effective silencing period. These embodiments are described in US Patent Application Pub. No. 2011/0195123.

In other embodiments, a DDD used in methods and compositions of the present invention further comprises another active agent. In certain embodiments, the additional active agent is another RNAi agent, for example ALN-VSP (Alnylam Inc, Cambridge, Mass.). Other examples of additional active agents that may be used are chemotherapy drugs, for example mAB-based agents, cytotoxic drugs, and kinase inhibitors.

Biodegradable Matrices

In certain embodiments, the biodegradable matrix present in the drug delivery device comprises poly(lactic acid) (PLA). In other embodiments, the biodegradable matrix comprises poly(glycolic acid) (PGA). In other embodiments, the biodegradable matrix comprises both PLA and PGA (known as poly(lactic-co-glycolic acid) or PLGA). In other embodiments the matrix comprises a natural polymer comprising β-1-4)-linked D-glucosamine and N-acetyl-D-glucosamine In a more specific embodiment, the matrix comprises Chitosan (NCBI PubChem ID #71853).

Methods for making PLGA matrices that incorporate RNAi agents are well known to those skilled in the art. Exemplary methods are described in described in US Patent Application Pub. No. 2011/0195123, the contents of which are incorporated herein by reference—for example in Examples 1.1 and 1.2 thereof.

In more specific embodiments, the PLA/PGA ratio is at least 75:25, more preferably between 75:25 and 95:5 inclusive. In other embodiments, the ratio is between 75:25 and 85:15 inclusive. In yet other embodiments, the ratio is no more than 25:75, more preferably between 25:75 and 5:95 inclusive. In other embodiments, the ratio is between 25:75 and 15:85 inclusive.

In other embodiments, the polymer comprises both PLA and PEG (poly(ethylene glycol)).

In other embodiments, tri-block PLA-PCL-PLA is used to form the matrix. PCL denotes poly-caprolactone.

In other embodiments, Poly(D,L-lactide) (DL-PLA), poly (D,L-glycolide), or poly(D,L-lactide-co-glycolide) is used, each of which is considered a separate embodiment.

Design of biodegradable controlled drug-delivery millimeter-scale DDD containing PLA, PGA, PEG, and/or PCL to have a specified release profile is well within the ability of those skilled in the art in light of the present disclosure. For example, general principles applicable to nano-scale and micro-scale particle carriers containing PLA, PGA, PEG, and/or PCL are described inter alia in Makadia and Siegel; and Park et al.

In another embodiment, the polymer is a polymer described in paragraphs 0076-0078 of US Patent Application Pub. No. 2011/0195123, the contents of which are incorporated herein by reference.

In other embodiments, the biodegradable matrix further comprises an additive for modulating hydrophilic-hydrophobic interactions; in other embodiments for enabling dispersion of the drug and eliminating aggregation; in other embodiments for preserving the drug in hot-temperature or cold-temperature storage conditions, for example 55° C. and −20° C., respectively; in other embodiments for facilitating creation of cavities in the implant that affect to drug diffusion from the matrix. Hydrophilic-hydrophobic interactions may cause aggregation of the active substance in cases of hydrophilic active substances, such as siRNA, incorporated within a hydrophobic polymer, resulting in aggregation during production or subsequently when the device is implanted into the body of a subject and it is subjected for example to hydrolysis. Non-limiting examples of such additives are open monosaccharides, for example mannitol; disaccharides such as trehalose; sorbitol; and other cyclic monosaccharides such as glucose, fructose, galactose and disaccharides such as sucrose. The above additives that are chiral may be in the form of the D-enantiomer, the L-enantiomer, or a racemic mixture. In other embodiments, more than one additive is present.

In other embodiments, the biodegradable matrix further comprises an additive for preserving the drug within the implant after implantation against low pH. The microenvironment in the implant interior tends to be acidic. Unlike chemotherapy, the pH should preferably be maintained above a threshold. For example while doxorubicin is stable in an acidic environment, with minimal hydrolytic degradation within a pH range of 3 to 6.5, RNAi agents can degrade at pH <3. In more specific embodiments, this additive may be selected from bicarbonate and carbonate, for example sodium bicarbonate and sodium carbonate. In some embodiments, one or more additives against decrease of pH are included in the matrix to control the degradation of the polymer, typically degradation by hydrolysis, thereby to control the release. Such an additive is designed with or without regard to the drug. Non limiting examples include magnesium carbonate, calcium carbonate, calcium hydroxyapatite, sodium bicarbonate and in general salts. In some embodiments, the salt distribution within the polymeric matrix is non-homogenous. In some embodiments, the salt distribution is lower toward the matrix surface and higher toward the center. For example, in some embodiments the concentration of salt in the center is at least 20% higher than the concentration at the matrix edge.

Suitable Release Profiles

In preferred embodiments, a device of the present invention is designed to release the active agent in a controlled fashion. It will be apparent to those of skill in the art, in light of the knowledge in the art taken together with the information provided herein, that the PLA:PGA ratio, the design of the polymer end group, for example a capped terminal end group and an uncapped carboxylic end group, the composition and additives, the molecular weight (MW) of the polymer, and the surface-to-volume ratio of the implant may be adjusted to achieve a particular release profile. For example, deviating the PLA:PGA ratio from 50:50, increasing the MW, or reducing the surface-to-volume ratio can increase the release time.

In other embodiments, the DDD of the present invention is designed with a particular release profile. One relevant parameter is the time point at which 90% of the active agent has been released.

In some embodiments, a DDD of the present invention releases 90% of the active agent over a time period between 3-24 months inclusive. In other embodiments, the time point of release of 90% of the active agent is between 3-12 months inclusive. In other embodiments, the time point is between 2-24 months inclusive. In other embodiments, the time point is between 2-15 months inclusive. Another relevant parameter is the percent of active agent released at a given time point. For example, in some embodiments, 80-99% inclusive of the active agent is released at the 3-month timepoint. In other embodiments, 80-99% inclusive of the active agent is released at the 2-month timepoint or the 4-month, 6-month, 9-month, 12-month, or 24-month timepoint, each of which is considered a separate embodiment.

Alternatively or in addition, in some embodiments no more than 30-50% of the active agent of a DDD of the present invention is released during the first 3 weeks.

Dosage and Drug Percentage

A DDD of the present invention may, in certain embodiments, contain at least 10 µg siRNA. In more specific embodiments, the amount is between 10-2000 µg (inclusive) siRNA per device. In still more specific embodiments, the amount is between 100-1500 (inclusive) µg, more preferably 150-1000 µg, more preferably 200-470 µg, more preferably 330-420 µg, more preferably 350-400 µg, more preferably 375 µg siRNA per device. In certain embodiments, 2-8 DDD, containing a total of 0.7-3.5 mg siRNA, are implanted into a tumor of a human subject. In certain embodiments 8-24 DDD are implanted into a tumor of a human subject, to improve distribution of the released drug within the tumor. In certain embodiments the number of DDDs per tumor is X, where X is between 8-24 inclusive, and the drug load of each DDD is 3.0/X mg +/−20% (for example X=10 and each DDD has 0.3 mg +/−20%).

In certain embodiments, the drug content of a device of the present invention is at least 10% by weight. Alternatively, the drug content of the device is at least 20%. In still other embodiments, the drug content of the device is at least 11%, at least 12%, at least 13%, at least 14%, at least 15%, at least 16%, at least 17%, at least 18%, at least 19%, at least 21%, at least 22%, at least 23%, at least 24%, at least 25%, at least 26%, at least 28%, or at least 30%, or at least 33%, or at least 36%, or at least 40%.

In another embodiment of a millimeter-scale DDD of the present invention, (a) the biodegradable matrix comprises PLGA, a sugar, (non-limiting embodiments of which are mannitol, trehalose, sucrose, and sorbitol), a pH modulating additive (non-limiting embodiments of which are sodium bicarbonate, magnesium carbonate and calcium carbonate); and (b) the nucleotide sequence of the sense strand of the RNAi agent is GUUGGAGCUGAUGGCGUAGdTdT (SEQ ID No: 41), and the sequence of the antisense strand is CUACGCCAUCAGCUCCAACdTdT (SEQ ID No: 42).

Some exemplary formulations of drug delivery devices of methods and compositions of the present invention are as follows, by weight: 16-32% siRNA, 7-11% Mannitol, 60-77% PLGA, and 0.5%-3% sodium bicarbonate and other excipients. In more specific embodiments, the DDD is 20% +/−5% siRNA by weight.

Additional Features

In other embodiments, a DDD of the present invention is non homogeneous. In other embodiments, a DDD of the present invention is multi-layered. In other embodiments, a DDD of the present invention comprises a biodegradable polymeric component attached to a bio-stable polymeric component and/or to a metallic component. In other embodiments, a DDD of the present invention is coated. A coating can be designed in some embodiments for a number of characteristics, including modulating the release rate or preventing protein stickiness during long-term storage. The coating in other embodiments comprises the same material or a similar material used to form the matrix. In other embodiments, the coating is a PLGA matrix containing no siRNA, or in other embodiments consists of PLA, or of PGA. In other embodiments, the coating further comprises another material, for example PEG.

Therapeutic Methods

Another aspect of the present invention provides a method of treating a patient having a solid tumor expressing a mutated K-ras protein, wherein the mutated K-ras protein comprises a mutation selected from G12D, G12V, G12A, G12S, G12C, G13D, and G13C, comprising the step of administering to the patient a millimeter-scale DDD, wherein the DDD comprises:

A. A biodegradable matrix; and

B. An RNAi (RNA interference) agent incorporated within the biodegradable matrix, wherein the RNAi agent comprises a duplex region, and the nucleotide sequence of the duplex region of the sense strand consists of

```
a sequence selected from SEQ ID No: 1-7, namely
                                       (SEQ ID No: 1)
GUUGGAGCUGAUGGCG, (SEQ ID No: 2)
GUUGGAGCUGUUGGCG, (SEQ ID No: 3)
GUUGGAGCUGCUGGCG,
```

```
                                                    (SEQ ID No: 4)
GUUGGAGCUAGUGGCG, (SEQ ID No: 5)
GUUGGAGCUUGUGGCG, (SEQ ID No: 6)
GUUGGAGCUGGUGACG,
and (SEQ ID No: 7)
GUUGGAGCUGGUUGCG, either alone or followed by:
a sequence selected from: (i)
                                                    (SEQ ID No: 8)
UAGGCAAGAGUGCC
and (b) a 5'-fragment of 1-13 nucleotides
inclusive of SEQ ID No: 8.
```

In more specific embodiments, the DDD is any of the embodiments thereof mentioned herein, each of which is considered to be a separate embodiment. In still more specific embodiments, the biodegradable matrix of the DDD comprises PLGA, mannitol (for example D-mannitol), and sodium bicarbonate; the nucleotide sequence of the sense strand of the RNAi agent of the DDD is GUUG-GAGCUGAUGGCGUAGdTdT (SEQ ID No: 41), and the sequence of the antisense strand of the RNAi agent is CUACGCCAUCAGCUCCAACdTdT (SEQ ID No: 42). In more specific embodiments, the DDD contains 16-32% siRNA by weight, 7-11% Mannitol, and 60-77% PLGA, +0.5%-3% sodium bicarbonate and other excipients. In more specific embodiments, the DDD is 20% +/−5% siRNA by weight.

Another aspect of the present invention provides a method of treating a patient having a solid tumor expressing a K-ras protein containing a G12D mutation, comprising the step of administering to the patient a pharmaceutical composition comprising an RNAi agent, wherein the sequences of the sense and antisense strands of the RNAi agent are:

```
                                                    (SEQ ID No: 37)
5'-GUoUoGGAGCUGAUGGCGoUoAGdTdT;
and (SEQ ID No: 38)
5'-CUACGCCAUCAGCUCCAACdTdT,
respectively.
```

In other embodiments, the aforementioned method further comprises administration of a chemotherapy drug such as gemcitabine. In other embodiments, the method further comprises radiation treatment.

Another aspect of the present invention provides a method of treating a patient having a solid tumor expressing a K-ras protein containing a G12D mutation, comprising the step of administering to the patient a pharmaceutical composition comprising an RNAi agent, wherein the sequences of the sense and antisense strands of the RNAi agent are:

```
                                                    (SEQ ID No: 39)
5'-GUoUGGAGCoUGAoUGGCGoUAG;
and (SEQ ID No: 40)
5'-CoUACGCoCAUoCAGCUCoCAAC,
respectively.
```

In other embodiments, the aforementioned method further comprises administration of a chemotherapy drug such as gemcitabine. In other embodiments, the method further comprises radiation treatment.

In other embodiments, the solid tumor treated by a method of the present invention is selected from pancreatic tumor, colon tumor, and lung tumor. In more specific embodiments, the cancer is selected from pancreatic carcinoma, pancreatic ductal adenocarcinoma, small-cell lung carcinoma, and colorectal cancer. In even more specific embodiments, the cancer is pancreatic ductal adenocarcinoma. In some embodiments, the tumor is an inoperable tumor; alternatively, it is an operable tumor.

In some preferred embodiments, a device is implanted intratumorally. In still other embodiments, the device is implanted into the vicinity of the tumor. In more specific embodiments, in the case of a well-defined solid tumor, several devices are spaced within the tumor volume. In yet other embodiments, several devices are implanted along a needle cavity within the tumor. In still other embodiments, the device or devices are implanted such that they are not in a direct contact with the perimeter of the tumor. Alternatively, in the case of a poorly defined solid tumor, the device is inserted into an area believed to contain tumor cells.

In still other embodiments, a method of the present invention further comprises the step of administering an anti-cancer agent to the patient. In more specific embodiments, the anti-cancer agent comprises a pyrimidine analogue, non-limiting examples of which are 5-azacytidine, 5-aza-2'-deoxycytidine, 5-fluoro-uracil, 5-fluoro-deoxyuridine (floxuridine), and 5-fluorodeoxyuridine monophosphate. In more specific embodiments, the anti-cancer agent is an inhibitor of ribonucleoside-diphosphate reductase large subunit (EC 1.17.4.1), non-limiting examples of which are motexafin gadolinium (CHEBI: 50161); hydroxyurea; gemcitabine (2', 2'-difluorodeoxycytidine); elacytarabine (CP-4055; an ara-C-5'elaidic-acid-ester) and CP-4126, (CO 1.01; a gemcitabine-5'elaidic-acid-ester; Adema AD et al, Metabolism and accumulation of the lipophilic deoxynucleoside analogs elacytarabine and CP-4126. Invest New Drugs. 2011 Oct. 15. [Epub ahead of print]), and those described in WO2011062503, the contents of which are incorporated herein by reference. In even more specific embodiments, the anti-cancer agent comprises gemcitabine. In alternative embodiments, the anti-cancer agent is gemcitabine. In yet other embodiments, the anti-cancer agent is an EGFR tyrosine kinase inhibitor. In yet other embodiments, the anti-cancer agent comprises a thymidylate synthase inhibitor. In more specific embodiments, the anti-cancer agent comprises leucovorin (Folinic acid; 2-[[4-[(2-amino-5-formyl-4-oxo-1, 6,7,8-tetrahydropteridin-6-yl)methylamino]benzoyl]amino] pentanedioic acid). In yet other embodiments, the anti-cancer agent comprises irinotecan. In yet other embodiments, the anti-cancer agent comprises oxaliplatin. In still other embodiments, the anti-cancer agent comprises FOLFIRIN (5-fluorouracil, leucovorin, and irinotecan in combination). In still other embodiments, the anti-cancer agent is FOLFIRINOX (5-fluorouracil, leucovorin, irinotecan, and oxaliplatin in combination), or any combination of a subset of the four agents in FOLFIRINOX. In yet other embodiments, the anti-cancer agent comprises an EGFR tyrosine kinase inhibitor. In more specific embodiments, the anti-cancer agent is Erlotinib.

In some embodiments, the anti-cancer agent is administered to the patient after administration of the DDD. In more specific embodiments, the anti-cancer agent may be administered to the patient up to 10 days after administration of the DDD. Alternatively, the anti-cancer agent is administered to the patient simultaneously with administration of the DDD. In still other embodiments, the anti-cancer agent is administered to the patient before administration of the DDD. In yet other embodiments, the DDD is administered during ongoing administration of the anti-cancer agent. In still other embodiments, the anti-cancer agent is administered to the patient intratumorally, by a method such as injection and controlled release, or including in other embodiments administration from the same DDD.

In still other embodiments, a method of the present invention further comprises the step of administering radiation therapy to the patient. In some embodiments, the radiation is administered to the patient after administration of the DDD. In more specific embodiments, the radiation may be administered to the patient up to 10 days after administration of the DDD. Alternatively, the radiation is administered to the patient simultaneously with administration of the DDD. In still other embodiments, the radiation is administered to the patient before administration of the DDD. In yet other embodiments, the DDD is administered during ongoing administration of the radiation.

Pharmaceutical Compositions

In another embodiment, the present invention provides a pharmaceutical composition for treating a patient having a solid tumor expressing a mutated K-ras protein, wherein the mutated K-ras protein comprises a mutation selected from G12D, G12V, G12A, G12S, G12C, G13D, and G13C, said pharmaceutical composition comprising a millimeter-scale DDD, said DDD comprising:

A. A biodegradable matrix; and
B. An RNAi (RNA interference) agent incorporated within the biodegradable matrix, wherein the RNAi agent comprises a duplex region, and the nucleotide sequence of the duplex region of the sense strand consists of:

```
a sequence selected from SEQ ID No: 1-7, namely
                                         (SEQ ID No: 1)
GUUGGAGCUGAUGGCG, (SEQ ID No: 2)
GUUGGAGCUGUUGGCG, (SEQ ID No: 3)
GUUGGAGCUGCUGGCG, (SEQ ID No: 4)
GUUGGAGCUAGUGGCG, (SEQ ID No: 5)
GUUGGAGCUUGUGGCG, (SEQ ID No: 6)
GUUGGAGCUGGUGACG,
and (SEQ ID No: 7)
GUUGGAGCUGGUUGCG,
either alone or followed by:

a sequence selected from: (i)
                                         (SEQ ID No: 8)
UAGGCAAGAGUGCC
and (b) a 5'-fragment of 1-13 nucleotides
inclusive of SEQ ID No: 8.
```

In more specific embodiments, the DDD is any of the embodiments thereof mentioned herein, each of which is considered to be a separate embodiment. In still more specific embodiments, the biodegradable matrix of the DDD comprises PLGA, mannitol (for example D-mannitol), and sodium bicarbonate; the nucleotide sequence of the sense strand of the RNAi agent of the DDD is GUUG-GAGCUGAUGGCGUAGdTdT (SEQ ID No: 41), and the sequence of the antisense strand of the RNAi agent is CUACGCCAUCAGCUCCAACdTdT (SEQ ID No: 42).

In another embodiment, the present invention provides a pharmaceutical composition for treating a patient having a solid tumor expressing a K-ras protein containing a G12D mutation, and G13C, said pharmaceutical composition comprising an RNAi agent, wherein the sequences of the sense and antisense strands of the RNAi agent are:

```
                                         (SEQ ID No: 37)
5'-GUoUoGGAGCUGAUGGCGoUoAGdTdT;
and (SEQ ID No: 38)
5'-CUACGCCAUCAGCUCCAACdTdT,
respectively.
```

In other embodiments, the aforementioned pharmaceutical composition further comprises a chemotherapy drug such as gemcitabine. In other embodiments, the pharmaceutical composition is indicated as an adjunct for radiation.

In another embodiment, the present invention provides a pharmaceutical composition for treating a patient having a solid tumor expressing a K-ras protein containing a G12D mutation, and G13C, said pharmaceutical composition comprising an RNAi agent, wherein the sequences of the sense and antisense strands of the RNAi agent are:

```
                                         (SEQ ID No: 39)
5'-GUoUGGAGCoUGAoUGGCGoUAG;
and (SEQ ID No: 40)
5'-CoUACGCoCAUoCAGCUCoCAAC,
respectively.
```

In other embodiments, the aforementioned pharmaceutical composition further comprises a chemotherapy drug such as gemcitabine. In other embodiments, the pharmaceutical composition is indicated as an adjunct for radiation.

In another embodiment, the present invention provides use of a millimeter-scale DDD in the preparation of a medicament for treating a patient having a solid tumor expressing a mutated K-ras protein, wherein the mutated K-ras protein comprises a mutation selected from G12D, G12V, G12A, G12S, G12C, G13D, and G13C, wherein said DDD comprises:

A. A biodegradable matrix; and
B. An RNAi (RNA interference) agent incorporated within the biodegradable matrix, wherein the RNAi agent comprises a duplex region, and the nucleotide sequence of the duplex region of the sense strand consists of:

```
a sequence selected from SEQ ID No: 1-7, namely
                                         (SEQ ID No: 1)
GUUGGAGCUGAUGGCG, (SEQ ID No: 2)
GUUGGAGCUGUUGGCG, (SEQ ID No: 3)
GUUGGAGCUGCUGGCG, (SEQ ID No: 4)
GUUGGAGCUAGUGGCG,
```

-continued

GUUGGAGCUUGUGGCG, (SEQ ID No: 5)

GUUGGAGCUGGUGACG, (SEQ ID No: 6)
and

GUUGGAGCUGGUUGCG, (SEQ ID No: 7)
either alone or followed by:

a sequence selected from: (i)
UAGGCAAGAGUGCC (SEQ ID No: 8)
and (b) a 5'-fragment
of 1-13 nucleotides inclusive of SEQ ID No: 8.

In more specific embodiments, the DDD is any of the embodiments thereof mentioned herein, each of which is considered to be a separate embodiment. In still more specific embodiments, the biodegradable matrix of the DDD comprises PLGA, mannitol (for example D-mannitol), and sodium bicarbonate; the nucleotide sequence of the sense strand of the RNAi agent of the DDD is GUUG-GAGCUGAUGGCGUAGdTdT (SEQ ID No: 41), and the sequence of the antisense strand of the RNAi agent is CUACGCCAUCAGCUCCAACdTdT (SEQ ID No: 42).

In another embodiment, the present invention provides use of an RNAi agent in the preparation of a medicament for treating a patient having a solid tumor expressing a K-ras protein containing a G12D mutation, wherein the sequences of the sense and antisense strands of the RNAi agent are:

5'-GUoUoGGAGCUGAUGGCGoUoAGdTdT; (SEQ ID No: 37)
and

5'-CUACGCCAUCAGCUCCAACdTdT, (SEQ ID No: 38)
respectively.

In other embodiments, the aforementioned RNAi agent and a chemotherapy drug such as gemcitabine are both used in the preparation of a medicament for treating a patient having a solid tumor expressing a K-ras protein containing a G12D mutation.

In another embodiment, the present invention provides use of an RNAi agent in the preparation of a medicament for treating a patient having a solid tumor expressing a K-ras protein containing a G12D mutation, wherein the sequences of the sense and antisense strands of the RNAi agent are:

5'-GUoUGGAGCoUGAoUGGCGoUAG; (SEQ ID No: 39)
and

5'-CoUACGCoCAUoCAGCUCoCAAC, (SEQ ID No: 40)
respectively.

In other embodiments, the aforementioned RNAi agent and a chemotherapy drug such as gemcitabine are both used in the preparation of a medicament for treating a patient having a solid tumor expressing a K-ras protein containing a G12D mutation.

In other embodiments, the solid tumor treated using a pharmaceutical composition of the present invention is selected from pancreatic tumor, colon tumor, lung tumor, brain, liver, kidney, prostate, melanoma, endometrial carcinoma, gastric carcinoma, renal carcinoma, biliary carcinoma, cervical carcinoma, and bladder carcinoma. In more specific embodiments, the cancer is selected from pancreatic carcinoma, pancreatic ductal adenocarcinoma, small-cell lung carcinoma, and colorectal cancer. In even more specific embodiments, the cancer is pancreatic ductal adenocarcinoma. In some embodiments, the tumor is an inoperable tumor; alternatively, it is an operable tumor.

In still other embodiments, a pharmaceutical composition of the present invention further comprises an anti-cancer agent. Alternatively, the pharmaceutical composition is indicated for administration in combination with an anti-cancer agent. In more specific embodiments, the anti-cancer agent is a pyrimidine analogue, non-limiting examples of which are mentioned herein. In even more specific embodiments, the anti-cancer agent comprises gemcitabine. In alternative embodiments, the anti-cancer agent is gemcitabine. In yet other embodiments, the anti-cancer agent is an EGFR tyrosine kinase inhibitor. In yet other embodiments, the anti-cancer agent comprises a thymidylate synthase inhibitor. In more specific embodiments, the anti-cancer agent comprises leucovorin (Folinic acid; 2-[[4-[(2-amino-5-formyl-4-oxo-1,6,7,8-tetrahydropteridin-6-yl)methylamino]benzoyl]amino]pentanedioic acid). In yet other embodiments, the anti-cancer agent comprises irinotecan. In yet other embodiments, the anti-cancer agent comprises oxaliplatin. In still other embodiments, the anti-cancer agent comprises FOLFIRIN (5-fluorouracil, leucovorin, and irinotecan in combination). In still other embodiments, the anti-cancer agent is FOLFIRINOX (5-fluorouracil, leucovorin, irinotecan, and oxaliplatin in combination). In yet other embodiments, the anti-cancer agent comprises an EGFR tyrosine kinase inhibitor. In more specific embodiments, the anti-cancer agent is Erlotinib.

In some embodiments, the anti-cancer agent is administered to the patient after administration of the DDD. In more specific embodiments, the anti-cancer agent may be administered to the patient up to 10 days after administration of the DDD. Alternatively, the anti-cancer agent is administered to the patient simultaneously with administration of the DDD. In still other embodiments, the anti-cancer agent is administered to the patient before administration of the DDD. In yet other embodiments, the DDD is administered during ongoing administration of the anti-cancer agent.

In yet other embodiments, a pharmaceutical composition of the present invention is indicated for administration with radiation therapy. In some embodiments, the radiation is administered to the patient after administration of the DDD. In more specific embodiments, the radiation may be administered to the patient up to 10 days after administration of the DDD. Alternatively, the radiation is administered to the patient simultaneously with administration of the DDD. In still other embodiments, the radiation is administered to the patient before administration of the DDD. In yet other embodiments, the DDD is administered during ongoing administration of the radiation.

EXPERIMENTAL DETAILS SECTION

Example 1 siG12D-DDD (drug delivery device) and siG12V-DDD Induce Necrosis in Capan-1 Subcutaneous Tumors Materials and Experimental Methods
Quantitation of CDC47-positive Cells Using the Ariol™ Platform
Six random windows, 0.6 mm² each, were selected from each slide and analyzed using Ariol™.

Implantation of Panc-1 Tumors

Mice were injected s.c. with 10×10⁶ Panc1-LUC tumor cells in a total volume of 100 μl PBS, or into the tail of the pancreas with 10⁶ cells in a total volume of 30 μl PBS.

Results

Capan-1 cells are tumor cells of human pancreatic cancer origin that express G12V-mutated K-ras and constitutively express Luciferase (LUC) gene were injected subcutaneously (s.c.) into Nude mice. 2.5 weeks later, mice were divided into 4 test groups: a). siG12D-DDD (4μg), b). siG12V-DDD (4 μg), c). Empty-DDD, and d). Untreated group.

Figure 1B:
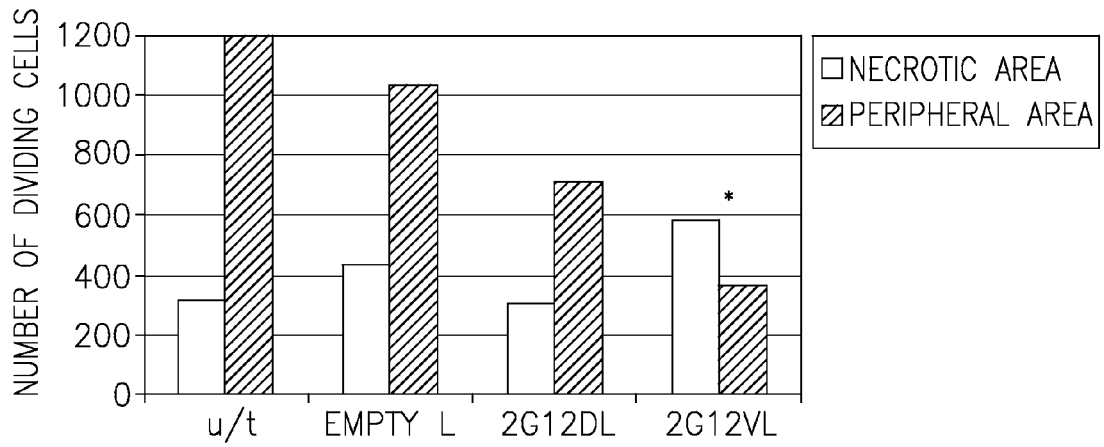

The DDD were implanted into the tumors. One month later, mice were sacrificed, and paraffin-embedded tumor sections were immuno-stained for CDC47, which detects all dividing cells. The necrotic (white-gray) areas were significantly larger in the siG12D and siG12V-DDD groups, relative to the other groups, in which they were nearly absent (FIG. 1A). Quantitation of CDC47-positive cells using the Ariol™ platform (Leica Biosystems) revealed a significantly lower number of dividing cells in the siG12V-DDD group than the other groups (FIG. 1B).

Thus, these particular RNAi agents in the context of the drug delivery devices were able to powerfully induce necrosis of the tumor cells.

Example 2 siG12D-DDD and siG12V-DDD Inhibit Growth of Subcutaneous Panc-1 Tumors and Extend Survival Panc1-LUC cells, which express G12D-mutated K-ras and constitutively express Luciferase, were injected subcutaneously into SCIDbg mice. siG12D-DDD and siLUC-DDD (control) were implanted into tumors. Tumor volume and Luciferase expression were used to track tumor growth.

Figure 2A:
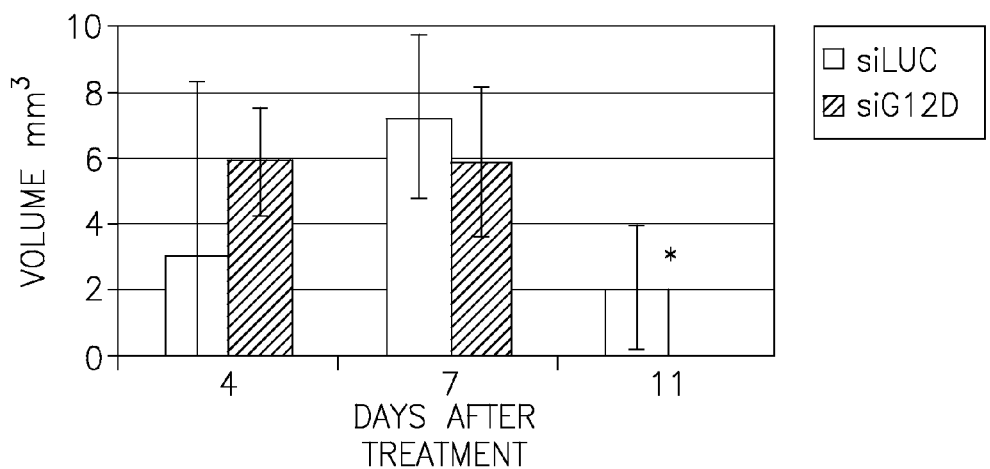
FIG. 2. A. Tumor volume in siG12D-DDD- and siLUC-DDD-treated mice. B. Representative H&E Histology samples from mice treated with siLUC-DDD (left 2 panels) or siG12D-DDD (right 2 panels). In one instance from the siG12D-DDD group, the tumor area around the DDD had shrunk. In another instance, the tumor tissue was replaced with connective tissue. An asterisk indicates a P-value of <0.05 relative to the siLUC control, by Student's T-test.
Figure 2B:
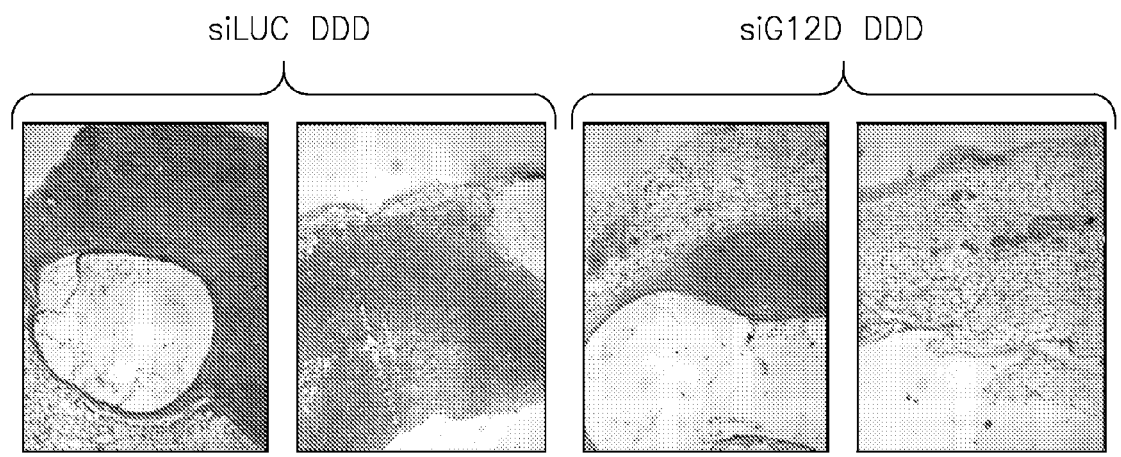

Tumors in the siG12D-DDD group began to shrink from day 7, at which point they were already smaller than the siLUC-DDD group, and disappeared by day 11 (FIG. 2A). Thus, the siG12D-DDD inhibited tumor growth. These differences were also evident in measurement of Luciferase levels and histology (FIG. 2B).

Figure 3:
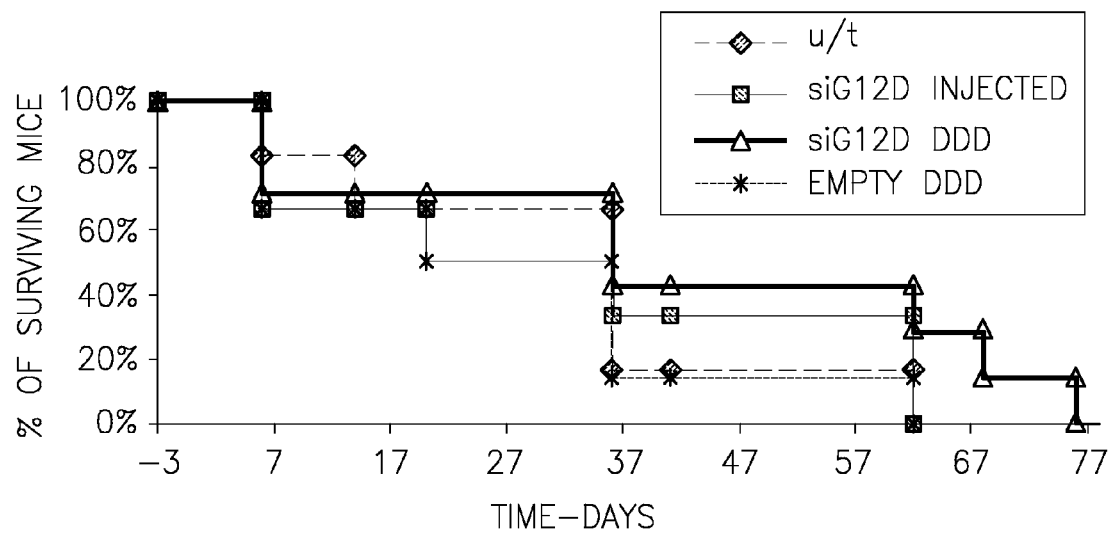
FIG. 3. Survival curve of SCIDbg mice with Panc1-LUC tumors over 41 days: Mice were treated with siG12D-DDD, Empty-DDD, or intraperitoneal injection of siG12D, or were untreated. The siG12D-DDD group had the highest survival rate.

In another experiment, 30 SCIDbg mice were injected s.c. with Panc1-LUC tumor cells, and were divided into 4 groups: (a) siG12D-DDD (12 μg siG12D per DDD)—2 DDD placed in each mouse; (b) empty DDD—2 DDD placed in each mouse; (c) 4 μg siG12D in 200 μl PBS injected intraperitoneally (i.p.) on a weekly basis; and (d) untreated. Tumor development was measured by caliper and Luciferase measurements. Mice treated with siG12D-DDD had the highest survival rate (42.86%), in comparison with the empty DDD (14.29%), siG12D IP injection (33.33%) and untreated (16.67%) (FIG. 3). The difference in survival was statistically significant ($p<0.05$ compared to the other 3 groups).

Similar results were seen in a survival study with 60 Nude mice injected with Capan-1-LUC tumors.

Thus, these particular siG12D RNAi agents in the context of the drug delivery devices were able to achieve in vivo tumor regression and extend survival of mice with pancreatic tumors. Moreover, the effect was greater than that achieved with repeated injection of siRNA.

Example 3 siG12D-DDD Exhibit High Tolability

To test the tolerability of the DDD, low-dose (25 μg) and high-dose (375 μg) DDD were implanted in mice to determine whether the device interacts with the surrounding tissue. The mice selected were healthy, with no immune suppression, and the tissue selected was subcutaneous, known to be highly immune-responsive. No difference in immune reaction was observed between the two doses, showing the high tolerability of the devices.

Example 4

Human trial of siG12D DDD

A Phase I clinical trial of escalating doses of siG12D-DDD was conducted. 4 patients in Cohort I were treated with a single 0.025-mg-DDD. Cohort II patients (#5-8) received two 0.375-mg DDDs (0.75-mg in total). Patients in Cohort III received eight 0.375-mg DDDs (3.0-mg in total). One patient (#9) so far has been enrolled for this Cohort; recruitment is ongoing.

No adverse events or flu-like syndromes definitely related to the DDD were observed. The implants were well tolerated.

Successive CT imaging in all patients during the 2 months following implantation and afterwards indicated a general trend of stable disease and no tumor progression. In patients #1 & #2 a necrotic area at the tumor center was observed (Table 1) CT scans after 2 months indicated 1 patient with PD from the Cohort I, and 1 patient of PR from Cohort II. Two more patients exhibited substantial tumor reduction: patient #3 exhibited a reduction of 21% in tumor size (axial) 2.5 months after DDD placement, and patient #9 exhibited a reduction of 25% in tumor coronal size after 2 months. (Patient #1 was withdrawn from the study, as the patient was discovered to have preexisting metastatic disease, based on a CT scan of on day 1 [prior to insertion of the DDD].

TABLE 1

Evaluation of patients using the Response Evaluation Criteria In Solid Tumors (RECIST) criteria (Padhani et al). CT analysis of nine patients, using the RECIST criteria

|  | 2 week | 3 week | 4 week | 2 month | 3 month | 4 month | 5 month | 8 month | Dose | Does |
|---|---|---|---|---|---|---|---|---|---|---|
| patient 1 | Omitted |  |  |  |  |  |  |  | Low | 25 ug |
| patient 2 |  | SD |  | PD |  | PD | PD | PD | Low | 25 ug |
| patient 3 |  | SD | SD | SD |  |  |  |  | Low | 25 ug |
| patient 4 |  |  |  | SD | SD |  |  |  | Low | 25 ug |
| patient 5 |  | SD |  | SD |  |  |  |  | Mid | 750 ug |
| patient 6 | SD |  |  | SD |  |  |  |  | Mid | 750 ug |
| patient 7 |  | SD |  | SD |  |  |  |  | Mid | 750 ug |

TABLE 1-continued

Evaluation of patients using the Response Evaluation
Criteria In Solid Tumors (RECIST) criteria (Padhani et al).
CT analysis of nine patients, using the RECIST criteria

|  | 2 week | 3 week | 4 week | 2 month | 3 month | 4 month | 5 month | 8 month | Dose | Does |
|---|---|---|---|---|---|---|---|---|---|---|
| patient 8 |  | PR | PR |  |  |  |  |  | Mid | 750 ug |
| patient 9 |  | SD | SD |  |  |  |  |  | High | 3000 ug |

PD = Progressive Disease, where the long diameter (LD) is increased by more than 20%; SD = stable disease; PR = Partial response, where LD is reduced by 30% or more).

Figure 4:
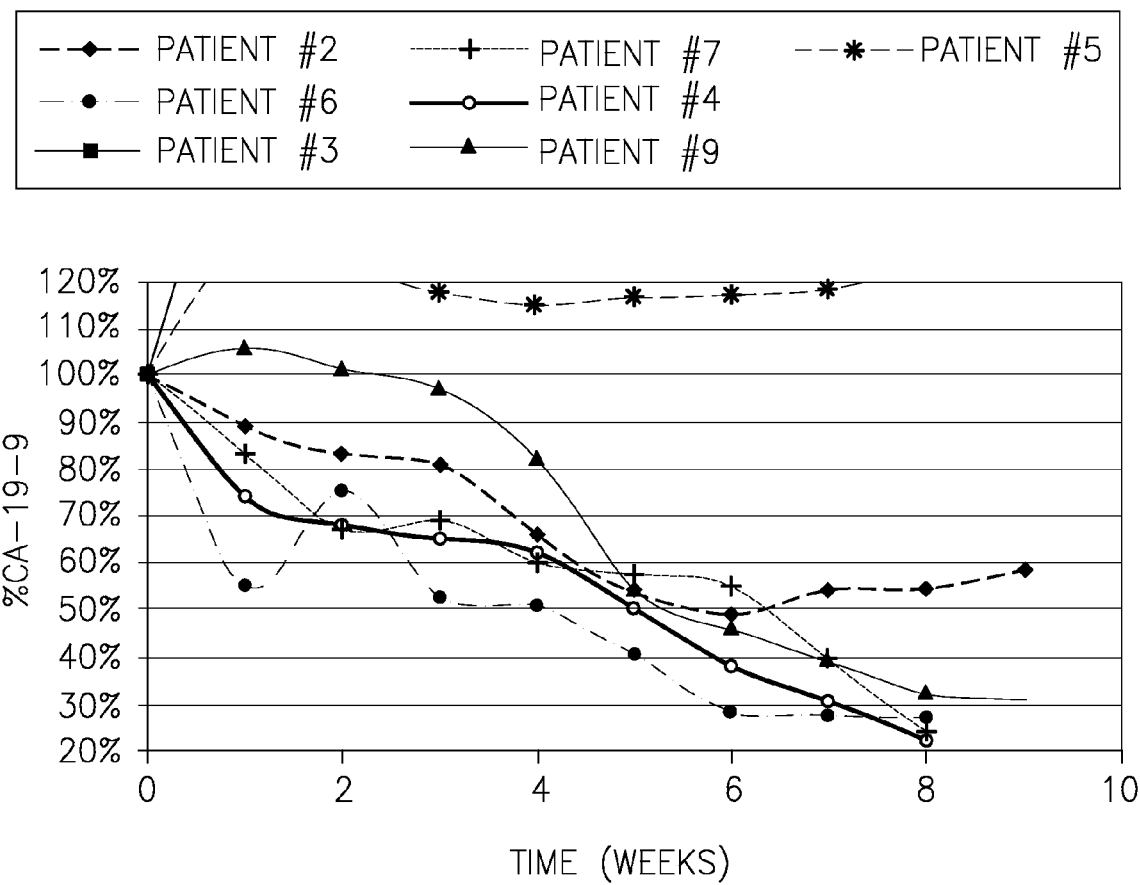
FIG. 4. Plot showing CA19-9 marker levels following insertion of siG12D-DDD intratumorally in humans. In 5/7 patients a significant reduction in CA19-9 marker levels was observed. In Cohort I, patients #2 and #4 showed reductions of 42% and 78%, respectively. Patients #6 and #7 from Cohort II showed reductions of 73% and 76%, respectively. Finally, CA19-9 values of patient #9 from Cohort III decreased by 71%.

In addition, six patients, namely #2, #3, #4, #6, #7 & #9, exhibited signs of efficacy based on readings of the tumor marker CA19-9 (FIG. 4). Specifically, CA19-9 levels decreased by 46% in Patient #2, 12% over the week following implantation, and an additional 78% in the following months, after patient started receiving Gemcitabine. In Patient #3, DDD implantation halted the increase in CA19-9 levels during the week after implantation. In Patient #4 exhibited a total reduction of 77% in CA19-9 values, 32% during the week after implantation and an additional 45% in the following weeks. Patient #4 exhibited a total reduction of 73%, 45% within the week after implantation and start of Gemcitabine treatment and an additional 28% during the following weeks. Patient #7 exhibited a total reduction of 76% after implantation and Gemcitabine treatment. Patient #9 exhibited a slight increase of 10% during the week after implantation, but during the following weeks the level declined by 69%.

Example 5

2'-OMe Modification of siG12D

Materials and Experimental Methods
Stability Studies

1-μl of modified siRNA was incubated at with 9-μl 50% human serum, at 37° C. The incubation was stopped at various time points (0 min, 10 min, 30 min, 4h, 24h, 1 week, 2 weeks and 4 weeks) by the addition of 10 μl sample buffer and freezing at −70° C. siRNA degradation was evaluated using urea-acrylamide gel-electrophoresis. Gels were stained with ethidium bromide, and band intensity was measured using Image Gauge™ software. Stability was evaluated by calculating the ratio between the intensity at each time point vs. the 0-min time point. Values were classified into five stability groups: Level 0: very unstable; 95-100% degraded; Level 1: unstable; 75-95% degraded; Level 2: medium stability; 50-75% degraded; Level 3: stable; 25-50% degraded; Level 4: very stable. 0-25% degraded.

Viability Studies

Panc1-luc cells were seeded in 96-well plate ($0.5 \times 10^4$ cells/well) to 70% confluence and were transfected with siRNAs. 120 hrs later, a 6-hr viability test was performed using the XTT assay. The indicated 4 levels of staining, namely 1, 2, 3, and 4 as shown in the last column of FIG. 6, related to levels of efficacy.

Results siG12D was modified with 2'-oxymethyl ("2'-OMe") at various positions, as set forth in Table 2 below.

TABLE 2

2-O-Methyl modifications of siG12D. "o"
denotes 2-O-Methyl modification.

| Ref. no. | Sequences | SEQ ID NOs |
|---|---|---|
| 1 | Sense: 5' GUoUGGAGCoUGAoUGGCGoUAGdTdT<br>Anti-sense: 5' CoUACGCoCAUoCAGCUCoCAACdTdT | 43-44 |
| 2 | Sense: 5' GUoUoGGAGCoUoGAoUoGGCGoUoAGdTdT<br>Anti-sense: 5' CoUACGCoCAUoCAGCUCoCAACdTdT | 45-46 |
| 3 | Sense: 5' GUoUoGGAGCoUoGAoUoGGCGoUoAGdTdT<br>Anti-sense: 5' CUACGCCAUCAGCUCCAACdTdT | 47-48 |
| 4 | Sense: 5' GUoUoGGAGCUGAUGGCGoUoAGdTdT<br>Anti-sense: 5' CUACGCCAUCAGCUCCAACdTdT | 37-38 |
| 5 | Sense: 5' GUoUoGGAGCUGAUGGCGoUoAGdTdT<br>Anti-sense: 5' CUoACGCCAUCAGCUCCAoAoCdTdT | 49-50 |
| 6 | Sense: 5' GUoUoGGAGCUGAUoGGCGoUoAGdTdT<br>Anti-sense: 5' CUoACGCoCAUCAGCUCCAoAoCdTdT | 51-52 |
| 7 | Sense: 5' GoUoUoGGAGCoUoGAoUoGGCGoUoAGdTdT<br>Anti-sense: 5' CUACGCCAUCAGCUCCAACdTdT | 53-54 |
| 8 | Sense: 5' oGUoUoGoGAoGCoUGoAUoGGoCGoUAoGdTdT<br>Anti-sense: 5' CoUAoCGoCCoAUCAGCoUCoCAoACdTdT | 55-56 |

TABLE 2-continued

2-O-Methyl modifications of siG12D. "o"
denotes 2-O-Methyl modification.

| Ref. no. | Sequences | SEQ ID NOs |
|---|---|---|
| 9 | Sense: 5' oGUoUGoGAoGCoUGoAUoGGoCGoUAoG<br>Anti-sense: 5' CoUAoCGoCCoAUCAGCoUCoCAoAC | 57-58 |
| 10 | Sense: 5' GoUoUoGGAGCoUoGoAoUoGGCGoUoAG<br>Anti-sense: 5' CUACGCCAUCAGCUCCAAC | 59-60 |
| 11 | Sense: 5' GoUoUoGGAGCoUoGoAoUoGGCGUAG<br>Anti-sense: 5' CUACGCCAUCAGCUCCAAC | 61-62 |
| 12 | Sense: 5' oGoUoUoGGAGCoUoGoAoUoGGCGUAoG<br>Anti-sense: 5' CUACGCCAUCAGCUCCAAC | 63-64 |
| 13 | Sense: 5' oGoUoUGGAGCoUoGoAoUoGGCGoUoAoG<br>Anti-sense: 5" CUAoCoGoCCAUCAGCoUoCoCAAC | 65-66 |
| 14 | Sense: 5' GUoUGGAGCoUGAoUGGCGoUAG<br>Anti-sense: 5' CoUACGCoCAUoCAGCUCoCAAC | 39-40 |
| 15 | Sense: 5' GoUoUoGGAGCoUoGoAoUoGGCGoUoAG<br>Anti-sense: 5' CoUACGCoCAUCAGCUCoCAAC | 67-68 |

Figure 5:
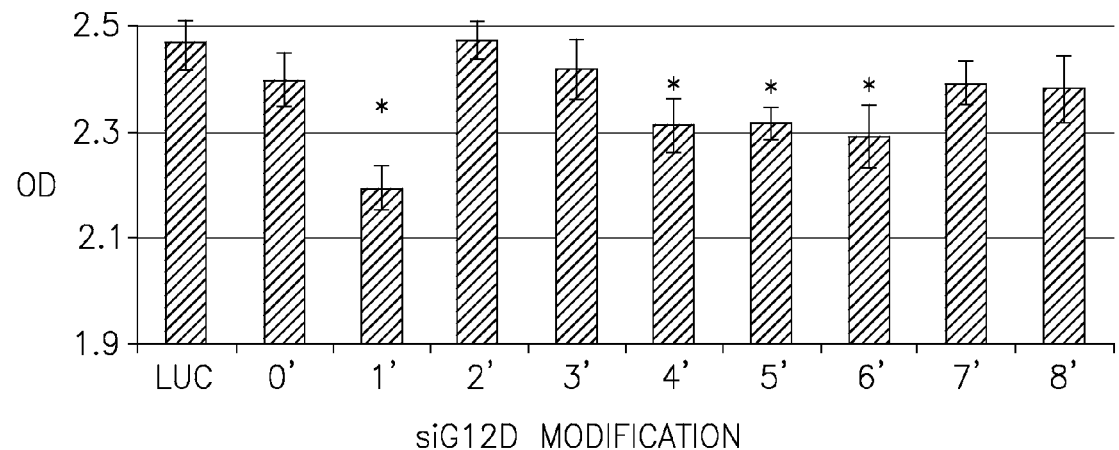
FIG. 5. Plot showing effect of various OMe-modified-siG12D #1-8 (top panel) and #9-15 (bottom panel) on viability of Panc1-luc cells. Higher OD levels indicate higher viability and therefore weaker effect. 0' denotes unmodified siG12D. siRNA against Luc and GFP are included as controls. An asterisk indicates a P-value of <0.05 relative to unmodified siG12D, by Student's T-test.
Figure 5:
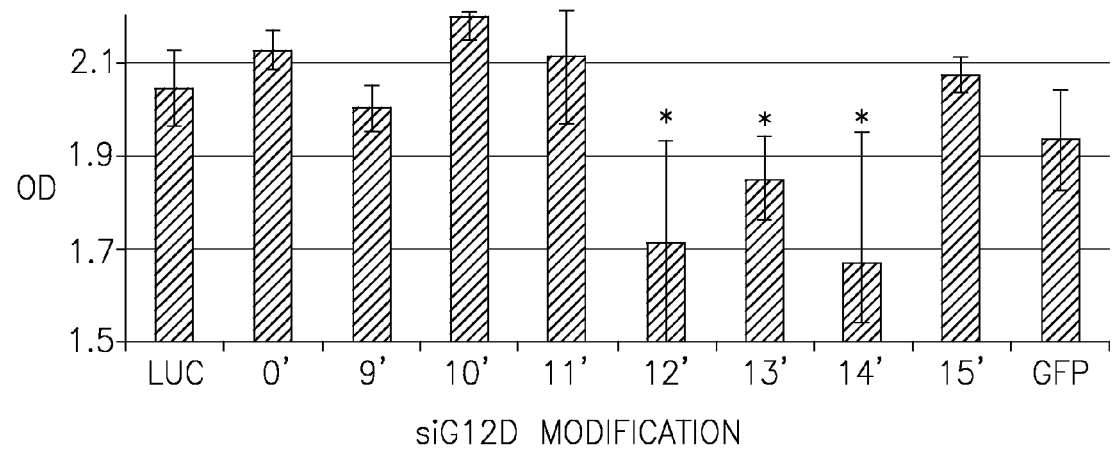
Figure 7:
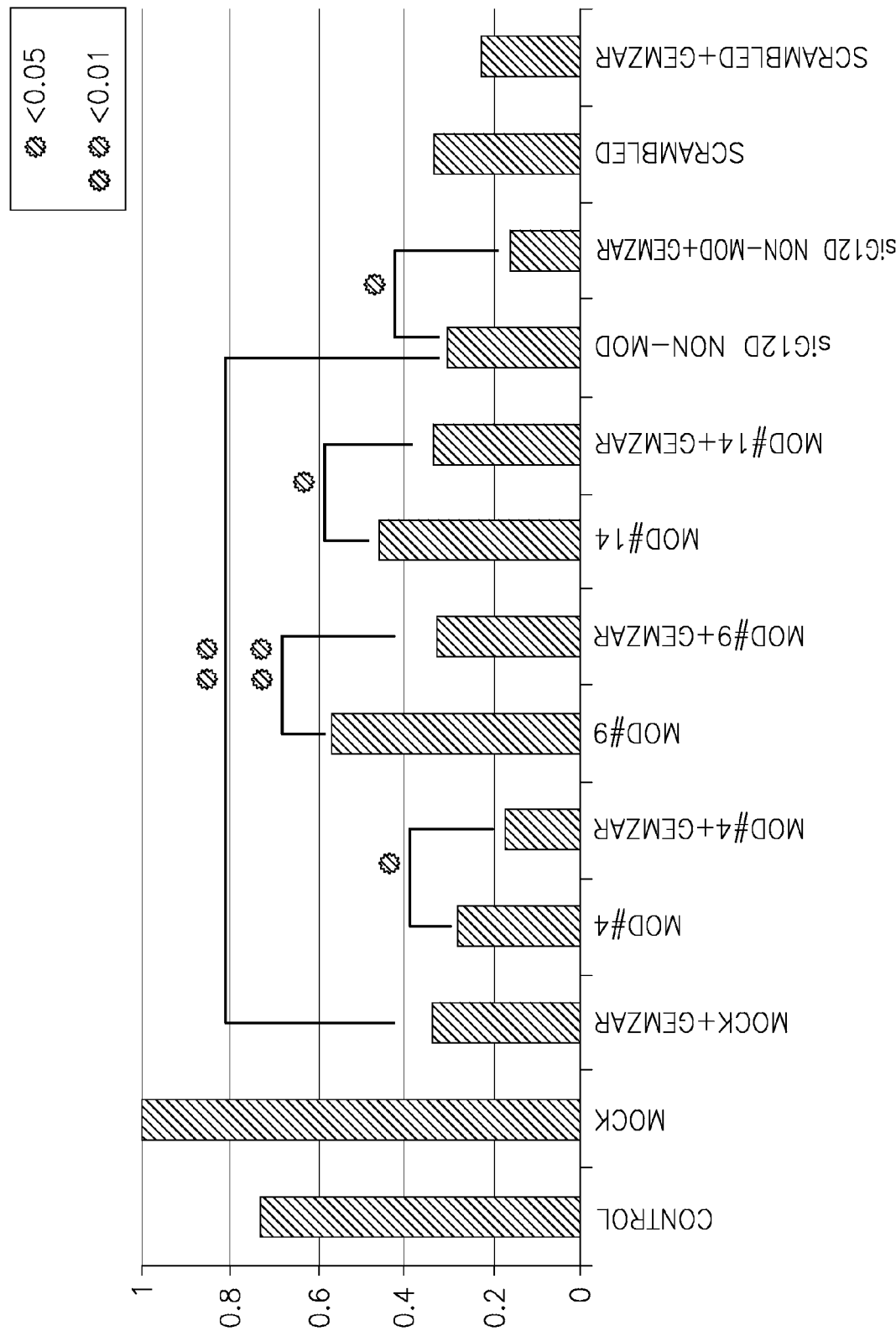
FIG. 7. Gemzar® enhances siG12D-DDD effect. Panc1 cells were transfected using Lipofectamine™ with unmodified and modified siG12D and a scrambled (non-targeting) siRNA control molecule or were mock transfected (no siRNA). Cell viability was assessed 72 hrs post-transfection by the Methylene Blue (MB) test. Additional groups were transfected as described above, followed by 1 hr of treatment with 10 µM Gemzar®. The numbers 1-4 in the last column relate to the percent of inhibition of cellular growth, wherein the inhibition seen with the unmodified siRNA was assigned the value of 100%. 4, 3, 2, and 1 refer respectively to 75-100%, 50-75%, 25-50%, and 0-25% of the inhibition seen with the unmodified siRNA.

The modified siRNA were tested for stability in serum, and several of them exhibited improved stability relative to the unmodified siRNA. Next, their effect on the viability of a pancreatic cancer cell line was tested in cell culture. Several of the modified siRNA exhibited improved efficacy relative to the unmodified siRNA (FIG. 5). The data is summarized in FIG. 6.

Example 6 in vivo Testing of 2'-OMe-modified siG12D Molecules

The efficacy of 2'-OMe-modified siG12D molecules is tested against tumors implanted in mice in a manner identical or similar to that described in the above description and Examples. Control groups include one or more of the following: (1) sham-operated; (2) empty DDD; and (3) unmodified siG12D DDD Improved efficacy against the tumors is indicative of enhanced anti-tumor activity as a result of the modification.

Example 7

Cholesterol Modification of siG12D

SiG12D is conjugated to cholesterol. The stability of the modified molecule is tested for stability in serum. Next, the effect of the molecule on the viability of pancreatic cancer cell line is tested in cell culture Improved stability and/or effect on viability is indicative of potentially enhanced anti-tumor activity as a result of the modification. In other experiments, ct-tocopherol is tested instead of cholesterol Example 8 in vivo Testing of Cholesterol-modified siG12D Molecules

The efficacy of cholesterol-modified siG12D molecules is tested against tumors implanted in mice in a manner identical or similar to that described in the above description and Examples. Control groups include one or more of the following: (1) sham-operated, (2) empty DDD, and (3) unmodified siG12D DDD Improved efficacy against the tumors is indicative of enhanced anti-tumor activity as a result of the modification.

Example 9

Effect of Specific Modified and Unmodified siG12D Molecules Alone and with Gemcitabine This study compared the effects on cell viability of specific modified and unmodified siG12D (using non-specific siRNA as a control), alone and combined with the chemotherapy drug Gemcitabine (Gemzar®).

Experimental procedure: Panc1 cells were transfected using Lipofectamine™ with unmodified and modified siG12D and a scrambled (non-targeting) siRNA control molecule or were mock transfected (no siRNA). Cell viability was assessed 72 hrs post-transfection by the Methylene Blue (MB) test. Additional groups were transfected as described above, followed by 1 hr of treatment with 10 µM Gemzar®. At the exemplary time point of 72h, Gemzar® enhanced the effect of siG12D by nearly 10%. Non-specific siRNA also reduced cell viability (probably via TLR3/interferon immune response pathway). Additionally, some modified siRNAs were able to achieve results comparable to un-modified siRNA. Other time points, for example 48h, 72h, 96h and 120h, may be utilized in additional studies.

Example 10

Assessment of the Effect of siG12D on the the Epithelial-to-mesenchymal Transition (EMT) Process in Pancreatic Cells In order to test the effect of administration of siG12D on the EMT process, pancreatic cells (such as Panc-1 or 6606 cells) are seeded in culture dishes for 12-72 hours, control and treated groups in the absence or presence of siG12D and an additional agent such as TGF-β (for induction of EMT). Experimental groups may include: 1. Untreated. 2. siG12D. 3. TGF-β. TGF-β+siG12D. Expression of mesenchymal markers (e.g. N-cadherin, Vimentin, S100A4, α-smooth-muscle cell actin [SMA]) and epithelial markers (e.g. E-cadherin, cytokeratin 8 or other cytokeratins, ZO-1, claudins, occludins, snail, slug, ZEB ½, and Twist½) is measured to track the EMT process.

Example 11

Effect of siG12D-DDD on Response of Tumors to Radiation Therapy

Pancreatic cancer cells that express G12D-mutated K-ras are injected IP (intraperitoneally) and/or subcutaneously into mice. After reaching an appropriate size, tumors are treated by implantation of a single or a few siG12D-DDD, alone or in combination with 1 or more courses of radiation beginning 0-30 days after DDD implantation. Tumor volumes measured to track tumor growth, and/or histology is performed at various timepoints. Groups of control mice receiving no treatment, siG12-DDD alone and or radiation alone may be included. In some experiments, pancreatic cancer cells that express both G12D-mutated K-ras and Luciferase are utilized, and the readout may include Luciferase measurements, for example as described in Example 2.

Example 12

Comparison of Chemotherapy Alone vs. Chemotherapy +siG12D-DDD

Patients with pancreatic cancer are administered 1 or more courses of Chemotherapy alone, for example Gemcitabine and/or FOLFIRINOX, or siG12D-DDD implantation followed by the same Chemotherapy treatment as the first group, beginning 0-120 days after DDD implantation. Disease progression is assessed, for example as described herein. siG12D-DDD is shown to be an effective adjunct to Chemotherapy.

Example 13

Comparison of Chemoradiotherapy vs. siG12D-DDD

Patients with pancreatic cancer are administered 1 or more courses of radiation or chemoradiotherapy (for example as described in Loeher et al 2011); or siG12D-DDD implantation with or without the same radiation or chemoradiotherapy used in the first group. Disease progression is assessed, for example as described herein. siG12D-DDD is shown to be safer, and comparable or superior in efficacy to radiation and or chemoradiotherapy.

With respect to the jurisdictions allowing it, all patents, patent applications, and publications mentioned herein, both supra and infra, are incorporated herein by reference.

In the claims, the word "comprise", and variations thereof such as "comprises", "comprising", and the like indicate that the components listed are included, but not generally to the exclusion of other components.

References

Brummelkamp et al, *Stable suppression of tumorigenicity by virus-mediated RNA Interference*. Cancer Cell September 2:243 (2002)

Fleming et al, *Molecular Consequences of Silencing Mutant K-ras in Pancreatic Cancer Cells: Justification for K-ras-Directed Therapy*. Mol Cancer Res 3(7):413-23 (2005).

Loeher et al, *Gemcitabine Alone Versus Gemcitabine Plus Radiotherapy in Patients With Locally Advanced Pancreatic Cancer: An Eastern Cooperative Oncology Group Trial* JOURNAL OF CLINICAL ONCOLOGY VOLUME 29 NUMBER 31 4105 (2011)

Makadia and Siegel, *Poly Lactic-co-Glycolic Acid (PLGA) as Biodegradable Controlled Drug Delivery Carrier*, Polymers 2011, 3, 1377-1397.

Morioka C Y et al, *Suppression of invasion of a hamster pancreatic cancer cell line by antisense oligonucleotides mutation-matched to K-ras gene*. In Vivo. 2005 May-Jun.; 19(3):535-8.

Normanno et al, *Implications for K-ras status and EgFR-targeted therapies in metastatic cRc*. Nat. Rev. Clin. Oncol. 6, 519-527 (2009).

Padhani A R, Ollivier L. *The RECIST (Response Evaluation Criteria in Solid Tumors) criteria: implications for diagnostic radiologists*. Br J Radiol 2001; 74: 983-986.

Park et al, *Biodegradable Polymers for Microencapsulation of Drugs*. Molecules 2005, 10: 146-161.

Réjiba et al, *K-ras oncogene silencing strategy reduces tumor growth and enhances gemcitabine chemotherapy efficacy for pancreatic cancer treatment*. Cancer Science 98(7): 1128-1136 (2007).

Singh et al, *A gene expression signature associated with "K-Ras addiction" reveals regulators of EMT and tumor cell survival*. Cancer Cell. 2009 Jun. 2;15(6):489-500.

Wang W et al, *Identification of effective siRNA against K-ras in human pancreatic cancer cell line MiaPaCa-2 by siRNA expression cassette*. World J Gastroenterol. 2005 Apr. 7;11 (13):2026-31.

The invention claimed is:

1. An RNAi (RNA interference) agent for treating a patient having a solid tumor expressing a mutated K-ras protein, comprising:

a sense strand and an antisense strand, wherein the sense strand and the antisense strand have sequences set forth in A, B, or C:

A.
(SEQ ID No: 37)
5'-GUoUoGGAGCUGAUGGCGoUoAGdTdT
and
(SEQ ID No: 38)
5'-CUACGCCAUCAGCUCCAACdTdT;

B.
(SEQ ID No: 39)
5'-GUoUGGAGCoUGAoUGGCGoUAG
and
(SEQ ID No: 40)
5'-CoUACGCoCAUoCAGCUCoCAAC;
OR C.
(SEQ ID No: 55)
5' oGUoUGoGAoGCoUGoAUoGGoCGoUAoGdTdT
(SEQ ID No: 56)
5' CoUAoCGoCCoAUCAGCoUCoCAoACdTdT, respectively, wherein "o" preceding a residue denotes a 2'-O-Methyl modification of the residue.

2. The RNAi agent of claim 1, wherein the RNAi agent is further modified with 2'-F.

3. A millimeter-scale drug delivery device (DDD), comprising:
A. a biodegradable polymeric matrix; and
B. an RNAi (RNA interference) agent incorporated within the biodegradable polymeric matrix, wherein the RNAi agent comprises a sense strand that has a sequence selected from SEQ ID Nos: 37, 39, and 55, and the RNAi agent further comprises an antisense strand whose sequence is selected from SEQ ID Nos: 38, 40, and 56 as set forth in A, B, or C:

A.
(SEQ ID No: 37)
5'-GUoUoGGAGCUGAUGGCGoUoAGdTdT
and
(SEQ ID No: 38)
5'-CUACGCCAUCAGCUCCAACdTdT;

B.
(SEQ ID No: 39)
5'-GUoUGGAGCoUGAoUGGCGoUAG
and
(SEQ ID No: 40)
5'-CoUACGCoCAUoCAGCUCoCAAC;
OR C.
(SEQ ID No: 55)
5' oGUoUGoGAoGCoUGoAUoGGoCGoUAoGdTdT
(SEQ ID No: 56)
5' CoUAoCGoCCoAUCAGCoUCoCAoACdTdT, respectively, wherein "o" preceding a residue denotes a 2'-O-Methyl modification of the residue.

4. The DDD of claim 3, wherein the DDD is 0.68 mm +/−0.45 mm in diameter.

5. The DDD of claim 3, wherein the DDD contains between 200-470 micrograms of RNAi agent per DDD.

6. The DDD of claim 3, wherein the RNAi agent is further modified with 2'-F.

7. The DDD of claim 3, wherein the RNAi agent is conjugated to a cholesterol or α-tocopherol moiety.

8. The DDD of claim 3, wherein the biodegradable polymeric matrix comprises PLA and PGA, and wherein the PLA and PGA are present in a ratio equal to or larger than 75:25, or equal to or smaller than 25:75.

9. The DDD of claim 3, further comprising an additive for modulating drug-polymer hydrophobic-hydrophilic interactions.

10. The DDD of claim 9, wherein the additive is selective from the group consisting of mannitol, trehalose, sorbitol, glucose, fructose, galactose, and sucrose.

11. The DDD of claim 3, further comprising a pH-modulating additive.

12. The DDD of claim 11, wherein the pH-modulating additive is selected from the group consisting of magnesium carbonate, calcium carbonate, calcium hydroxyapatite, and sodium bicarbonate.

* * * * *